US007052638B2

(12) United States Patent
Clarner et al.

(10) Patent No.: US 7,052,638 B2
(45) Date of Patent: May 30, 2006

(54) HOOK AND LOOP FASTENER

(75) Inventors: Mark A. Clarner, Concord, NH (US);
George A. Provost, Litchfield, NH (US); William L. Huber, Epsom, NH (US)

(73) Assignee: Velcro Industries B.V., Curacan (AN)

( * ) Notice: Subject to any disclaimer, the term of this patent is extended or adjusted under 35 U.S.C. 154(b) by 0 days.

(21) Appl. No.: 10/455,240

(22) Filed: Jun. 4, 2003

(65) Prior Publication Data

US 2004/0031130 A1    Feb. 19, 2004

Related U.S. Application Data

(60) Continuation-in-part of application No. 10/163,169, filed on Jun. 4, 2002, which is a continuation-in-part of application No. 09/870,063, filed on May 30, 2001, now Pat. No. 6,708,378, which is a division of application No. 09/231,134, filed on Jan. 15, 1999, now Pat. No. 6,248,276, which is a continuation-in-part of application No. 09/808,395, filed on Mar. 14, 2001.

(60) Provisional application No. 60/295,937, filed on Jun. 4, 2001.

(51) Int. Cl.
*B29C 47/88* (2006.01)
(52) U.S. Cl. ................ 264/167; 264/210.2; 264/210.5; 264/280; 264/296
(58) Field of Classification Search ............... 264/167, 264/280, 234, 296; 428/100; 24/452, 446
See application file for complete search history.

(56) References Cited

U.S. PATENT DOCUMENTS 2,820,877 A     1/1958  Oates, Jr. .................... 219/25

(Continued)

FOREIGN PATENT DOCUMENTS

WO       WO 02/45536 A    6/2002

(Continued)

OTHER PUBLICATIONS

US 6,129,874, 10/2000, Buzzell et al. (withdrawn)

*Primary Examiner*—Mark Eashoo
(74) *Attorney, Agent, or Firm*—Fish & Richardson P.C.

(57) ABSTRACT

Forming a fastener component having heads constructed to engage loops formed e.g. of fibers of a mating component, comprises forming, from a thermoformable material, a preform product having a sheet-form base and an array of preform stems integrally molded with and extending from the base to corresponding terminal ends, by a process having a machine direction and a cross-machine direction. Each molded stem has at least two terminal features spaced from one another in the cross-machine direction, the features having a transverse shape about which engaging fibers can bend, the features having a thickness of about 0.25 mm (0.010 inch) or less, preferably about 0.20 mm (0.008 inch), and for personal care products and the like preferably about 0.1 mm (0.004 inch) or less. The terminal ends of the features are heated to a predetermined softening temperature and the terminal ends are contacted to reform the terminal ends to form heads therefrom that overhang the sheet-form base sufficiently to engage loops.

Also shown are molded stems that have at least two terminal features spaced from one another in the machine direction; molded preform having substantially parallel side surfaces on all sides, e.g., of "M" or crossed "M" profile of substantially thin fin or crossed thin fin form of molded stems that carry upwardly directed, spaced apart prongs.

Preforms are shown having at least three prongs along at least one coordinate. Each prong of a group of at least two neighboring prongs is coalesced to form a head or all prongs of a stem are coalesced to form a single head.

57 Claims, 32 Drawing Sheets

U.S. PATENT DOCUMENTS

| | | | |
|---|---|---|---|
| 3,138,841 A | 6/1964 | Naimer | 24/204 |
| 3,191,255 A | 6/1965 | Nealis | 24/205.12 |
| 3,192,589 A | 7/1965 | Pearson | 24/204 |
| 3,266,113 A | 8/1966 | Flanagan, Jr. | 24/204 |
| 3,312,583 A | 4/1967 | Rochlis | 161/62 |
| 3,399,425 A | 9/1968 | Lemelson | 18/10 |
| 3,408,705 A | 11/1968 | Keyser et al. | 24/204 |
| 3,527,001 A | 9/1970 | Kleemeier et al. | 51/358 |
| 3,557,407 A | 1/1971 | Lemelson | 18/10 |
| 3,590,109 A * | 6/1971 | Doleman et al. | 264/167 |
| 3,718,725 A | 2/1973 | Hamano | 264/163 |
| 3,808,648 A | 5/1974 | Billarant et al. | 24/204 |
| 4,001,366 A | 1/1977 | Brumlik | 264/147 |
| 4,169,303 A | 10/1979 | Lemelson | 24/204 |
| 4,290,174 A | 9/1981 | Kalleberg | 24/204 |
| 4,454,183 A | 6/1984 | Wollman | 428/92 |
| 4,775,310 A | 10/1988 | Fischer | 425/308 |
| 4,794,028 A | 12/1988 | Fischer | 428/100 |
| 4,880,589 A | 11/1989 | Shigemoto et al. | 264/216 |
| 4,894,060 A | 1/1990 | Nestegard | 604/391 |
| 5,076,793 A | 12/1991 | Aghevli et al. | 434/196 |
| 5,077,870 A | 1/1992 | Melbye et al. | 24/452 |
| 5,396,687 A | 3/1995 | Osterman | 24/449 |
| 5,505,747 A | 4/1996 | Chesley et al. | 51/297 |
| 5,607,635 A | 3/1997 | Melbye et al. | 264/169 |
| 5,657,516 A | 8/1997 | Berg et al. | 24/204 |
| 5,679,302 A | 10/1997 | Miller et al. | 264/167 |
| 5,713,111 A | 2/1998 | Hattori et al. | 24/452 |
| 5,749,129 A | 5/1998 | Murasaki et al. | 24/452 |
| 5,755,015 A | 5/1998 | Akeno et al. | 24/452 |
| 5,781,969 A | 7/1998 | Akeno et al. | 24/452 |
| 5,792,408 A | 8/1998 | Akeno et al. | 264/284 |
| 5,800,845 A | 9/1998 | Akeno et al. | 425/224 |
| 5,845,375 A | 12/1998 | Miller et al. | 24/452 |
| 5,868,987 A | 2/1999 | Kampfer et al. | 264/280 |
| 5,879,604 A | 3/1999 | Melbye et al. | 264/167 |
| 5,884,374 A | 3/1999 | Clune | 24/446 |
| 5,913,482 A | 6/1999 | Akeno | 24/452 |
| 5,933,927 A | 8/1999 | Miller et al. | 24/452 |
| 5,951,931 A | 9/1999 | Murasaki et al. | 264/167 |
| 5,953,797 A | 9/1999 | Provost et al. | 24/452 |
| 5,981,027 A | 11/1999 | Parallada | 428/120 |
| 6,000,106 A * | 12/1999 | Kampfer et al. | 24/452 |
| 6,039,911 A | 3/2000 | Miller et al. | 264/280 |
| 6,054,091 A | 4/2000 | Miller et al. | 264/442 |
| 6,127,018 A * | 10/2000 | Akeno et al. | 428/100 |
| 6,162,040 A | 12/2000 | Clune | 425/363 |
| 6,248,276 B1 | 6/2001 | Parallada et al. | 264/167 |
| 6,287,665 B1 | 9/2001 | Hammer | 428/100 |
| 6,627,133 B1* | 9/2003 | Tuma | 264/167 |
| 6,678,924 B1* | 1/2004 | Murasaki et al. | 24/452 |
| 6,708,378 B1* | 3/2004 | Parellada et al. | 24/452 |
| 2001/0018110 A1 | 8/2001 | Tuman et al. | 428/99 |
| 2002/0022108 A1* | 2/2002 | Krantz et al. | 428/100 |
| 2002/0069495 A1 | 6/2002 | Murasaki | |
| 2004/0033336 A1* | 2/2004 | Schulte | 428/100 |

FOREIGN PATENT DOCUMENTS

| | | |
|---|---|---|
| WO | WO 03/028499 A1 | 4/2003 |
| DE | 2 213 686 | 3/1972 |
| DE | 296 08 260 | 5/1996 |
| DE | 198 28 856 | 6/1998 |
| DE | 100.56.567 | 11/2000 |
| EP | 0 806 158 | 3/1997 |
| EP | 0 811 331 A2 | 12/1997 |
| EP | 0 811 332 | 12/1997 |
| GB | 2 279 106 | 12/1994 |
| GB | 2 349 354 | 11/2000 |
| JP | 4-286029 | 10/1922 |
| WO | WO 82/02480 | 8/1982 |
| WO | WO 92/04839 | 4/1992 |
| WO | WO 94/23610 | 10/1994 |
| WO | WO 98/14086 | 4/1998 |
| WO | WO 98/30381 | 7/1998 |
| WO | WO 98/57564 | 12/1998 |
| WO | WO 98/57565 | 12/1998 |
| WO | WO 99/10161 | 3/1999 |
| WO | WO 99/26507 | 6/1999 |
| WO | WO 00/41479 | 7/2000 |
| WO | WO 01/24654 | 4/2001 |

* cited by examiner

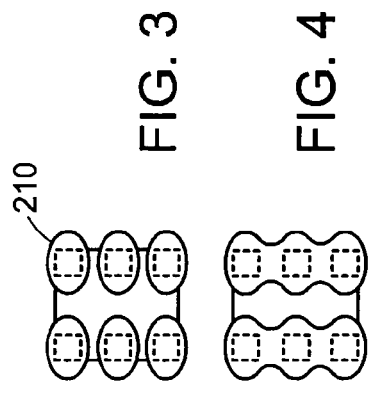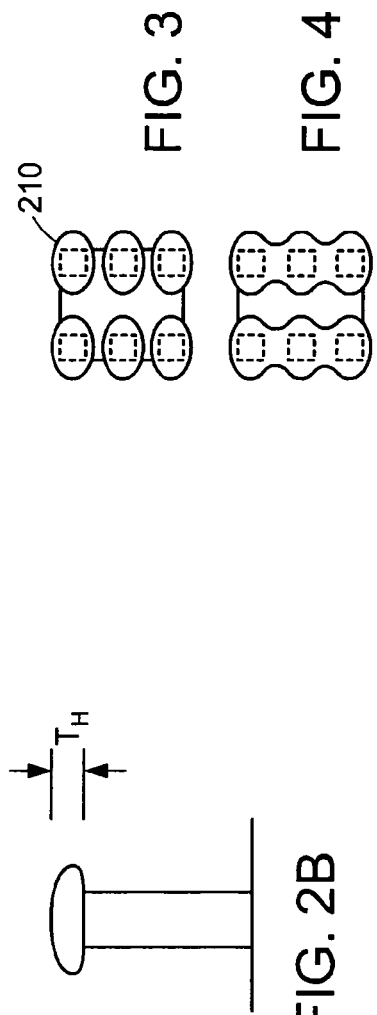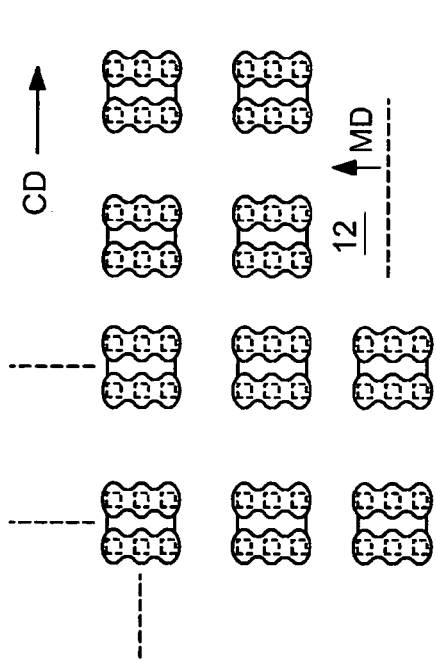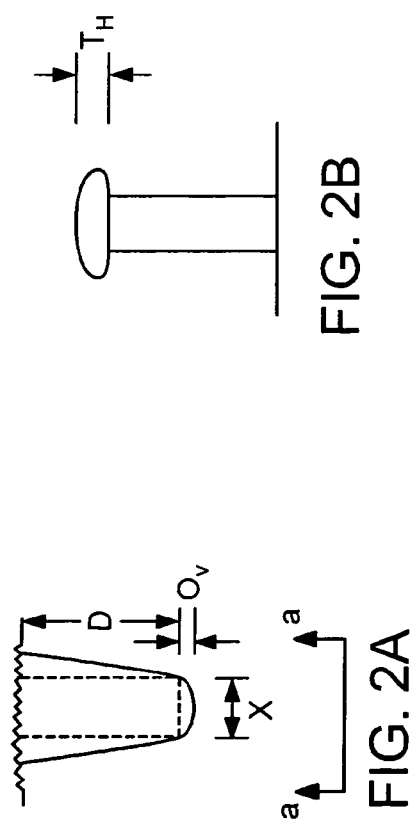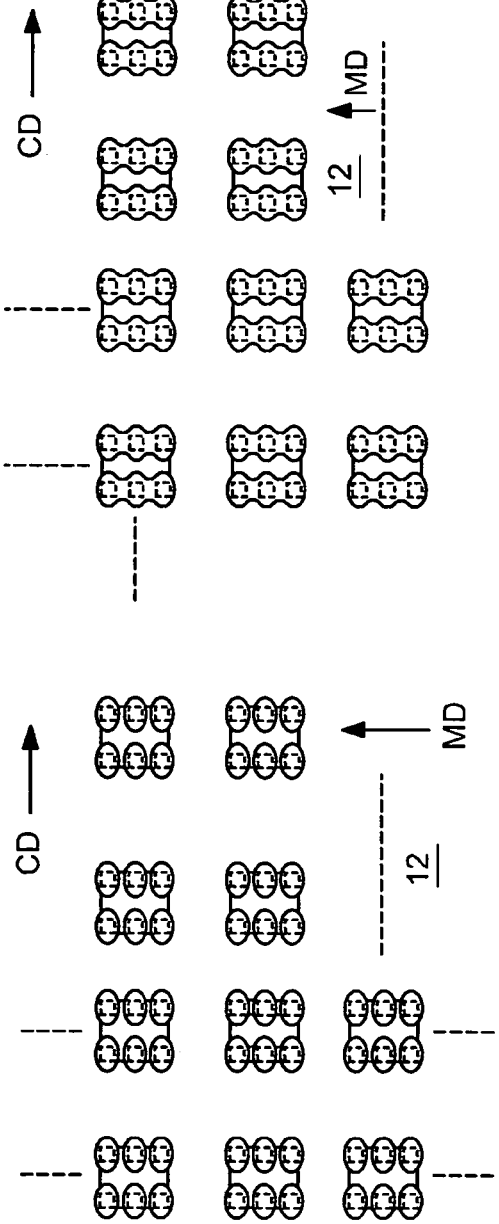

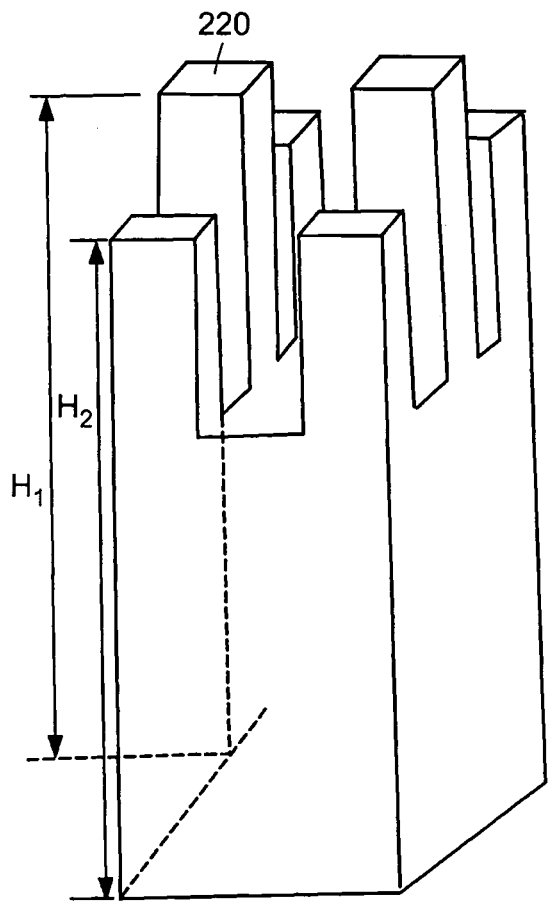
FIG. 18
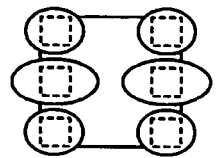
FIG. 19
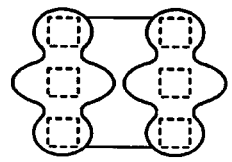
FIG. 20
FIG. 21
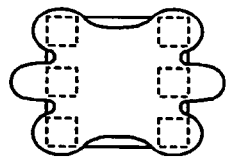
FIG. 22
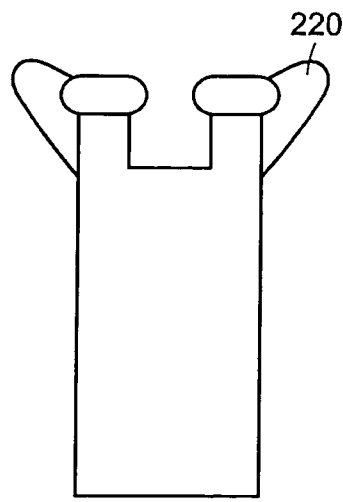
FIG. 23

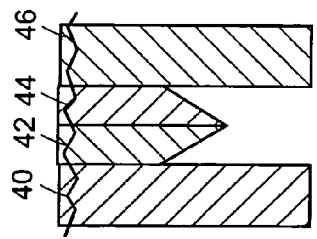
FIG. 34G
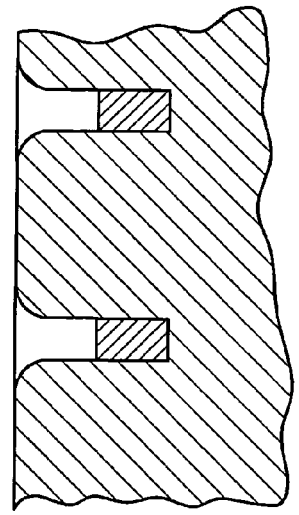
FIG. 34J
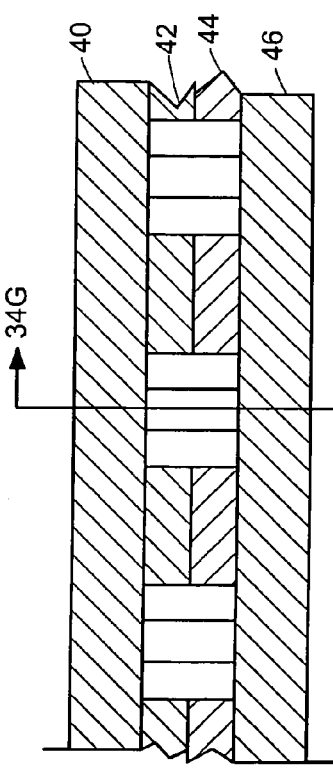
FIG. 34F
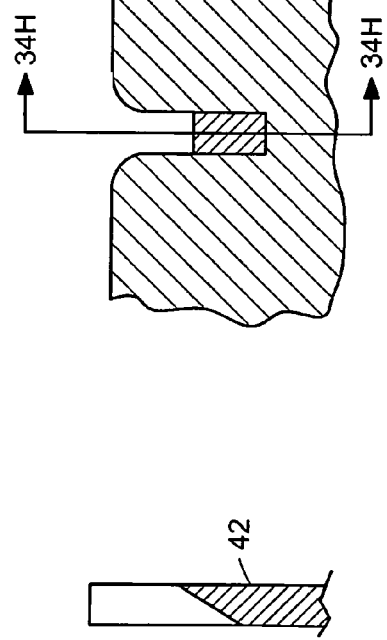
FIG. 34I
FIG. 34H

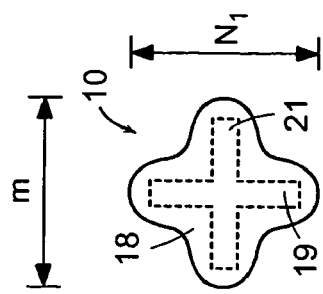
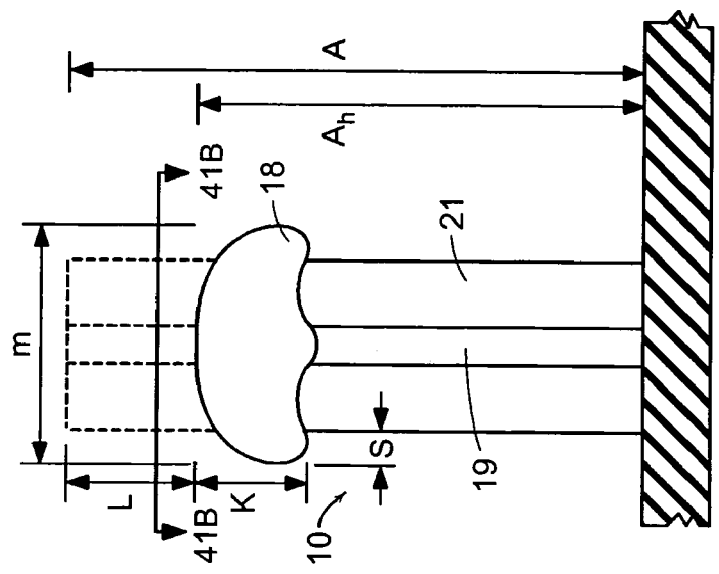
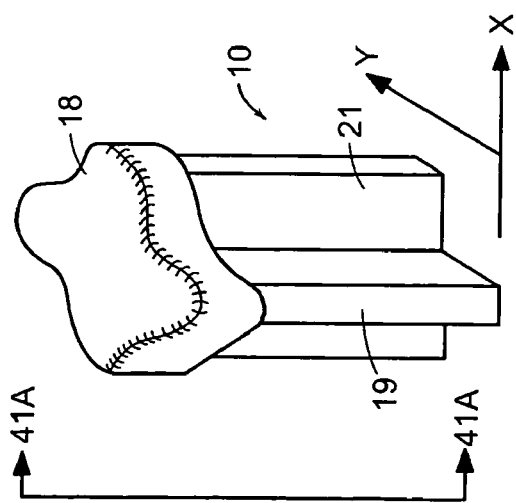

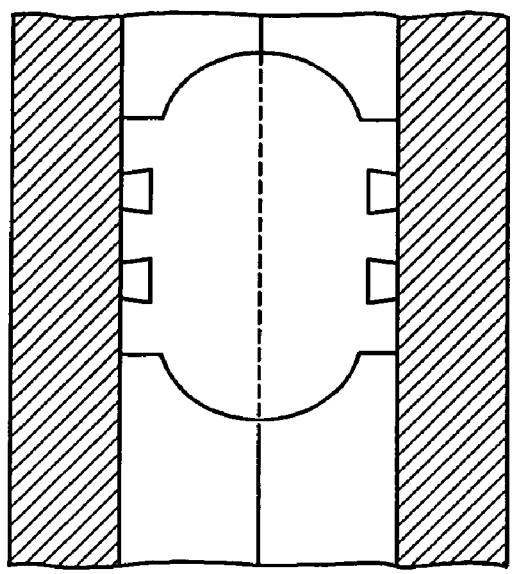
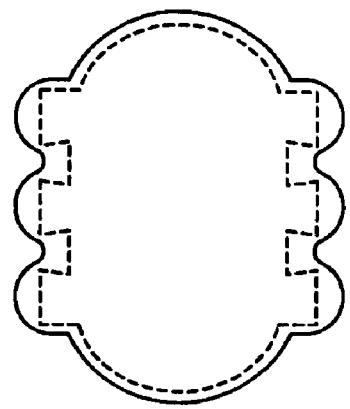
FIG. 52
FIG. 53
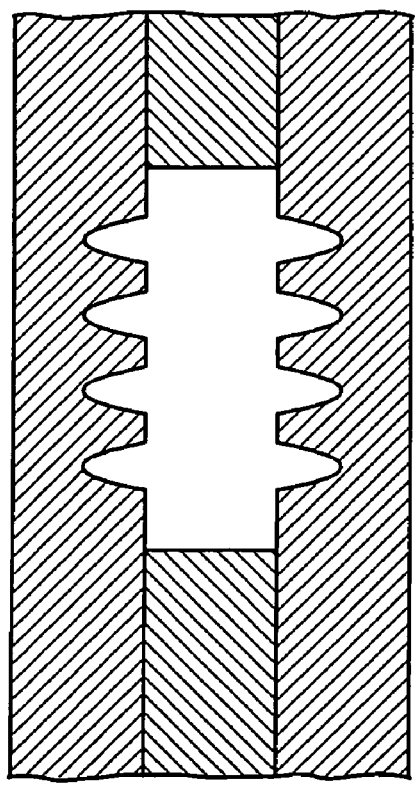
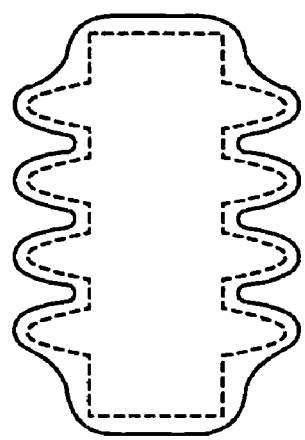
FIG. 54
FIG. 55

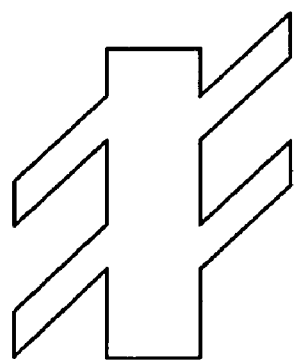
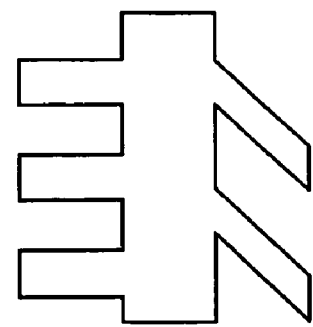
FIG. 69      FIG. 70
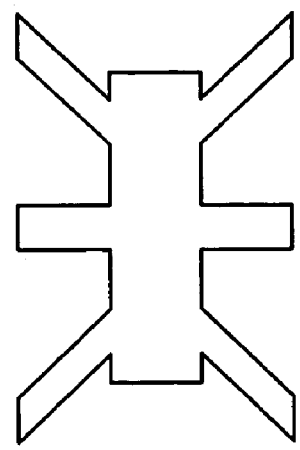
FIG. 71
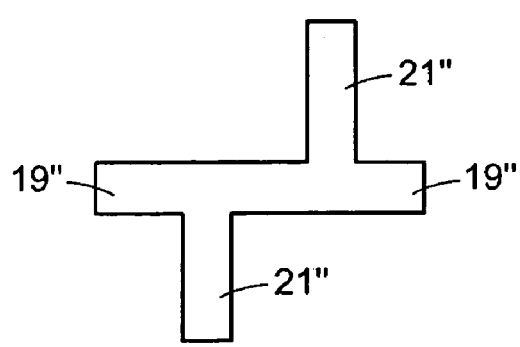
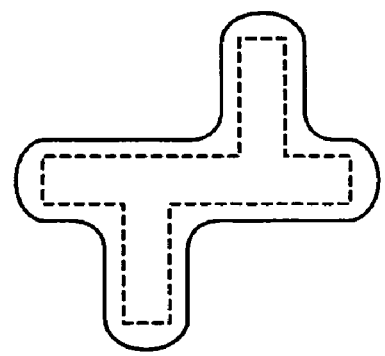
FIG. 72      FIG. 73

HOOK AND LOOP FASTENER

This application is a continuation-in-part of U.S. Ser. No. 10/163,169, filed Jun. 4, 2002, which claims priority from U.S. Provisional Application Ser. No. 60/295,937, filed Jun. 4, 2001. This application is also a continuation-in-part of U.S. Ser. No. 09/870,063, filed May 30, 2001, now U.S. Pat. No. 6,708,378 which is a divisional of U.S. Ser. No. 09/231,134, filed Jan. 15, 1999, now U.S. Pat. No. 6,248,276, which is a continuation-in-part of U.S. Ser. No. 09/808,395, filed Mar. 14, 2001.

TECHNICAL FIELD

This disclosure relates to touch fasteners commonly known as hook and loop fasteners. In many aspects it deals with the particular case in which hooks engage flexible loops such as are formed of fibers of thin nonwoven materials and the like.

BACKGROUND

The present invention relates to male fastener components that engage in openings of a female component, e.g. engage in openings of loops formed by fibers of a nonwoven female component. The invention more particularly relates to stem and head formations of the male elements that promote loop engageability and to methods and machines for their manufacture and their use.

There is a general need for male fastener components for hook and loop fasteners that provide good peel and shear strength properties in desired single or multiple directions and that are relatively inexpensive to manufacture. There is a specific need for low cost male fastener components that can function with low cost nonwoven loop materials.

There is also a need to be able to consistently and efficiently produce male fastener products having differing functional characteristics, using techniques that require limited changeover in basic tooling, yet allow for adjustments to produce the desired fastener characteristics.

Furthermore, it is especially desirable to extend the use of hook and loop fastening systems into fields of low cost products and still obtain good fastening performance. Examples include mid- and lowest-cost disposable diapers and sanitary products, disposable packaging for low price products, and disposable lowest cost surgical and industrial clothing and wraps, and single use medical and therapeutic devices. There are many other recognized low-cost product areas to which such fasteners would be applicable.

In particular it is desirable to obtain good engagement of the male member of the fastening systems with low cost nonwoven loop products that are characterized by their thinness and the low height to which their loop-defining fibers extend.

"Good engagement" in some instances means engaging a large percentage of hooks with low-lying loops. "Good engagement" in other applications often requires more, as in the case of fasteners for diapers, which require the hook component to exhibit strong "peel" resistance when engaged with thin, low cost loop materials. With such materials, the limited loop height does not permit significant transition of loading from the hook head to the hook stem during peeling action, as does occur with expensive loop products that have higher loop height. For this reason there are special problems to be addressed with hooks for thin loop structures in addition to the need to reduce the cost of the hook component and its tooling.

To explain the peel considerations more fully, in a hook and loop type fastener, "peel strength" is the resistance to stripping of one component from the other when a force normal to the mating surfaces is applied to the extremity of one of the components. Such peeling force on the component causes it to flex and progressively peel from the other. It is desirable to have peel strength in a hook and loop fastener that ensures that the closure does not release under normal forces of use but still permits the components to be separated when desired.

When the loop element is thin, as is usually the case for low-cost female fasteners, the individual loops are very short and low-lying. With application of a peel force, such loop exerts a force on the hook that is essentially perpendicular to the sheet-form base and parallel to the stem of the individual hooks. Consequently the force is applied primarily only to the heads of the hooks.

In contrast, when the loop element has a thick pile structure comprised of long individual loops, a loop must first be pulled out to its full length before it can exert significant force on a hook. As this occurs, the base webs to which the hooks and loops are attached are enabled to flex away from each other (see FIG. 1). Thus, at the point of separation of hooks from thick pile loops, the mated components are no longer face-to-face, and the angle at which a loop exerts its force on a hook is less than perpendicular. The longer the loop length, the more that angle diminishes. Thus, with a loop components having long loops, the force not only acts on the head of the hook, but also on its stem, and for very long loops, most of the resistance force is on the stem during peeling action.

However, for short loops, most of the resistance force is on the hook head, the consequence being that the hook head must be strong and provide much of the resistance to peel separation. Therefore, the use of thin and inexpensive loop components is to be expanded and improved, the hook head geometry must be improved to increase strength of engagement and produce an acceptable closure.

In many cases it is desirable to form the male hook members by molding an array of stems integrally (i.e. monolithically) with a common base, and subsequently post-treating the stems by a pressed formation step to form loop-engageable heads. In many instances it is desired to use continuous processes that act in a given machine direction, but to find a way to do this to achieve a hook product having good peel strength when the user applies peel forces at a substantial angle to the machine direction, in many cases at right angles, i.e. in the cross-machine direction.

SUMMARY

There are provided a method of forming a fastener component having heads constructed to engage loops formed e.g. of fibers of a mating component and products resulting from and characterized by the method. The method comprises forming, from a thermoformable material, a preform product having a sheet-form base and an array of preform stems integrally molded with and extending from the base to corresponding terminal ends, using a process having a machine direction and a cross-machine direction, with molded stems each having at least two terminal features spaced from one another in the cross-machine direction, these terminal features having a transverse shape about which engaging fibers can bend, the features having a thickness of about 0.25 mm (0.010 inch) or less, preferably about 0.20 mm (0.008 inch), and for personal care products and the like preferably about 0. 1 mm (0.004 inch) or less.

The terminal ends of these features are heated to a predetermined softening temperature while maintaining the sheet-form base and a lower portion of each stem at a temperature lower than the softening temperature, and the terminal ends are contacted with a contact surface that is at a predetermined forming temperature to reform the terminal ends to form heads therefrom that overhang the sheet-form base sufficiently to engage loops, the geometry and material of the preform product and the condition of reforming the terminal ends of the features being so related that the formed heads are capable of peel-resistant engagement with loops formed by fibers of thin or ultrathin nonwoven fabrics.

Preferred embodiments have one or more following features.

The stems up to the terminal ends of the features extend straight, do not overhang the base layer.

Each molded stem also has at least two terminal features spaced from one another in the machine direction.

The molded preform stems have substantially parallel side surfaces on all sides, preferably the parallel sides extending perpendicular to the sheet form base.

The molded stems are of substantially "M" or crossed "M" profile, or the molded stems are of substantially thin fin or crossed thin fin form, or the molded stems carry upwardly directed, spaced apart prongs that define said features.

Protrusions from the stem are in multiples, having in many cases a bifurcated or trifurcated appearance.

In the case that the prongs extend upwardly from a stem, one prong has dimensions different from another prong selected to form a different head shape, for instance, at least one prong has a terminal end spaced further from the base than another prong, and/or at least one prong has a transverse dimension different from another prong. Preferably, a stem has at least three prongs arranged along at least one coordinate, and a separate fiber-engaging head is formed on the terminal end of each prong, or head portions of a group of at least two neighboring prongs are coalesced to form portions of a single head, or head portions of all prongs of a stem are coalesced to form portions of a single head.

In certain preferred embodiments, transverse cross-sections of the prongs have a rectangular profile, while in other embodiments in transverse cross-section the prongs have a round profile.

The terminal ends of the features are heated by non-contact heating, e.g., the non-contact heat source comprises a convective heat source, preferably the convective heat source comprising a flame.

The preform stems and the features thereon are formed from a synthetic polymer, the polymer being molecularly unoriented.

The step of heating the terminal ends of the features to a predetermined softening temperature forms ball-like configurations at the terminal ends of the feature.

The temperature of the contact surface is sufficiently low that the thermoformable material does not adhere to the contact surface.

Water, water of combustion or steam or a spray of fine water molecules is introduced to the contact surface to provide a non-adhering condition.

In another method, preform members are provided having three or more prongs, or similar upright head forming features extending in one coordinate from a single stem, preferably there being at least two rows thereof in the other coordinate from that stem.

Other contributions of the invention are the unique fastener members per se as shown in the drawings and the preform members from which they are to be made, within the size ranges described in the specification.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A and 2B are respectively top and side views of a preform feature on the terminal end of which an overhanging loop-engaging head has been formed.

FIGS. 3–6 are top views of a set of loop-engageable fastener head portions made on a preform member of FIG. 2, the views showing varying degrees of head coalescence produced by respectively different head-forming conditions.

FIGS. 3A–6A are top views of arrays of loop-engageable fasteners corresponding, respectively, to the designs of FIGS. 3–6, the fasteners shown on a reduced scale.

FIG. 18 is a highly enlarged perspective view of another six-prong preform member having prongs of two different heights.

FIGS. 19–22 are respective top views of a set of loop-engageable fastener head portions made on a preform member of FIG. 18, illustrating varying degrees of head coalescence.

FIG. 23 is a side view of an alternative fastener product made from the preform member of FIG. 18.

FIG. 29 is a top view of a fastener made from the preform member of FIG. 28, while

FIG. 34F through FIG. 34J are various cross-sections taken through mold rings of the set as indicated, that define molds for molding the preform stem component of FIGS. 34C, D and E.

FIGS. 35–35E are views, corresponding to FIGS. 34–34E, of another embodiment, a modified M, and its preform element, while

FIG. 41 is a diagrammatic perspective view of an embodiment of a multi-lobed hook element, while FIG. 41A is a side view taken on lines 41A—41A of FIG. 41 and FIG. 41B is a top view taken on lines 41B—41B of FIG. 41A.

FIGS. 42 through 42B are views of a preform element employed in forming the hook element of FIG. 41, FIG. 42 being a diagrammatic perspective view of the molded preform element, FIG. 42a a vertical side view of the element and FIG. 42b a horizontal section view of the preform element taken on line 42B—42B of FIG. 42a.

FIG. 48 is a view similar to that of FIGS. 44 and 45, showing the tool rings in assembled relationship and FIG. 49 is a view similar to FIG. 48, but on more magnified scale showing two pairs of such rings assembled with spacer rings.

FIGS. 52 and 53, respectively, are top views of a six-feature fastener member and tooling for its preform.

FIGS. 54 and 55, respectively, are top views of an eight-feature fastener member and tooling for its preform.

FIGS. 68–72 are top views of multi-feature preform members that can be formed with tooling based on principles similar to the principles illustrated in FIG. 67.

FIG. 73 is a top view of a fastener member made from the preform member of FIG. 72.

DETAILED DESCRIPTION

Figure 1:
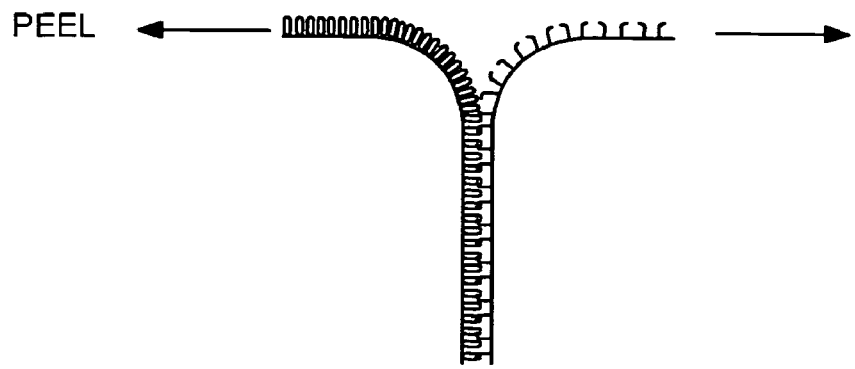
FIG. 1 is an illustrative side view of hooks engaged with a thick-pile loop material undergoing peeling action.
Figure 2:
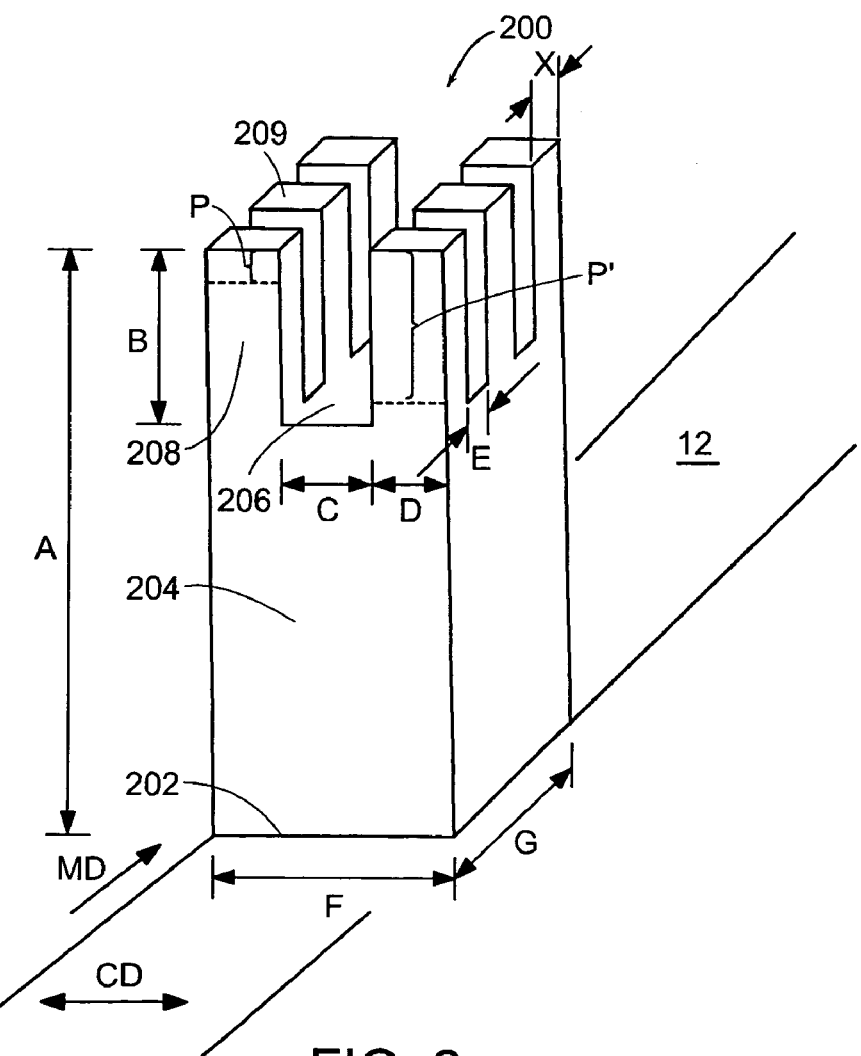
FIG. 2 is a highly enlarged perspective view of a single six-prong preform member molded integrally with a base layer.

Referring to FIG. 2, straight-sided preform member 200 of molded plastic resin extends upwardly from and is continuous with a plastic resin base layer 12 in a monolithic structure. The member 200 includes a stem base 202, a central solid stem portion 204, a stem top surface 206 and a plurality of parallel upwardly directed prongs 208 extending to respective terminal ends 209. The prongs have no overhang of the base, and all side surfaces of the stems and prongs are parallel (except for a small draft angle). In this embodiment, as shown, there is a 2 by 3 pattern of upwardly directed prongs, each prong having in transverse section (parallel to the base) a rectangular cross-sectional profile. In this profile, each prong is longer in the cross-machine direction than in the machine direction and hence is stiffer in that direction. There are on the single perform stem, 3 prongs aligned in the machine direction in each of two columns spaced apart in the cross-machine direction. Thus there are three sets of cross-machine-extending pairs of prongs. The prongs of each pair in this embodiment as shown are spaced further apart (in the cross machine direction) than the spacing between the pairs in the machine direction.

Figure 5:
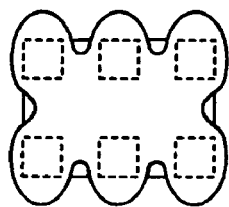
Figure 6:
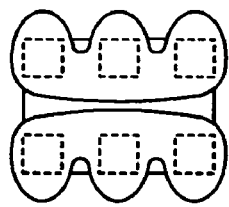
Figure 5A:
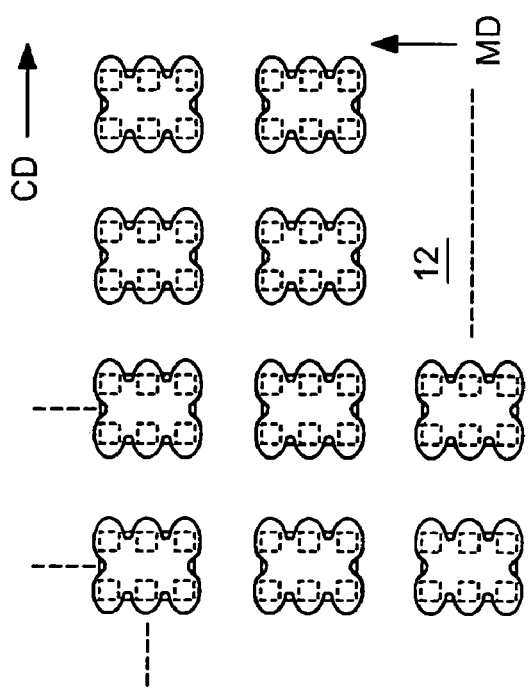
Figure 6A:
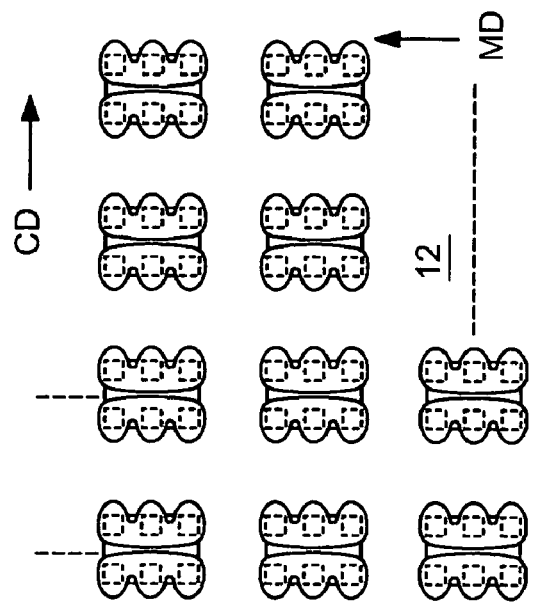

From this pronged preform member, individual heads 210 (e.g., FIG. 3) are formed by the application of appropriate heat and pressure to the terminal ends 209 of the prongs. By control of the heating and pressure parameters, the shape of loop-engaging heads 210 can be selectably formed to a desired conformation depending upon the particular fastening environment and fastening characteristics required. As illustrated in the embodiment of FIG. 3, with a limited amount of displacement by application of pressure to molten terminal ends of the prongs, individual fiber-engaging heads 210, FIG. 3, are formed having the appearance of headed teeth, with spaces between all adjacent teeth in which fibers may be engaged. Individual heads as they form can instead be forced to coalesce by heating the prongs further and/or applying a higher pressure and greater deformation to the heated prongs. In the embodiment of FIG. 4, sufficient heat and pressure has been applied to cause the resin of closest prongs, i.e., those in the machine direction, to merge, to produce two coalesced heads, each having three fiber-engaging knob-like features. In the embodiment of FIG. 5, further heating and pressure is effective to coalesce the heads of all prongs into a 6-lobed head. In the embodiment of FIG. 6, concentrated heating in the interior of the six prong set, relative to the exterior, forms a more rounded internal shape than that achieved in FIG. 4.

A large array of each of these fastener types creates a sheet-form fastener product such as those shown in FIGS. 3A–6A, respectively. In the arrays shown the fastener members are aligned in X, Y coordinates. For certain applications it is desirable instead to employ a staggered array.

A machine 100 for forming the fastening heads described above is shown in FIG. 7. A supply roll 102, 126 introduces a continuous supply of a stem-carrying base 12 into the machine 100. Stem-carrying base 12 is formed of a thermoformable polymer. In a previous manufacturing step, roll 102 was wound up as the take-up roll at a molding station (not shown) where stems with prongs were integrally molded onto base 12. The molding station may include a mold roll having a plurality of mold cavities provided by aligned plates. The molding station will be described in further detail later.

The supply roll 102 is unwound by drive mechanism 106, which conveys stem-carrying base 12 into optional pre-heating area 108 which raises the temperature of the stem-carrying base 12 to a pre-heat temperature that is above room temperature, but much lower than the Vicat softening temperature of the polymer. This pre-heating allows the stems with prongs to be heated to a predetermined softening temperature more quickly during the next step of the process.

Next, the base 12 moves to heating device 110, which heats the prongs. If only a small portion P (FIG. 2) of the prongs are heated by heating device 110, structures like that shown in FIGS. 3 and 4 result. Heating a larger portion P' of the prongs, leads to coalescing of the individual heads, as shown in FIGS. 5 and 6. Portion P (or P') is heated to a softening temperature, typically a temperature that is greater than or equal to the Vicat softening temperature of the thermoformable polymer and then portion P (or P') can be formed into a desired head shape. The remainder of the stem is not heated, and remains at a temperature that is less than the softening temperature, preferably at least 10% less.

Figure 8:
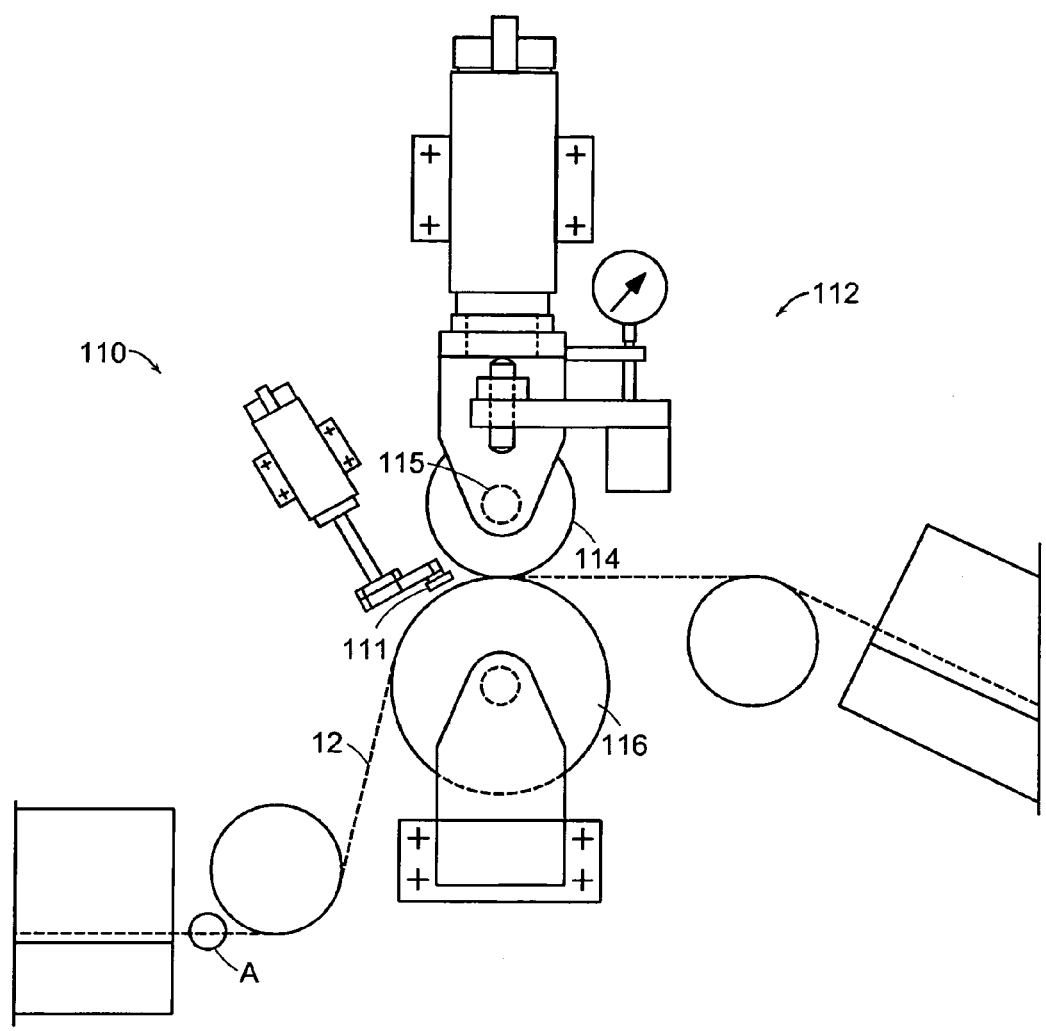
FIG. 8 is a side view of a portion of the apparatus of FIG. 7 at larger scale.

To ensure that only portion P (or P') is heated to the softening temperature, it is preferred that heating device 110 include a non-contact heat source 111 (FIG. 8) that is capable of quickly elevating the temperature of material that is very close to the heat source, without raising the temperature of material that is relatively further away from the heat source. Suitable non-contact heat sources include flame heaters, electrically heated nichrome wire, and radiant heater blocks. To heat portion P (or P') to the softening temperature without contact, the heat source typically must be at a relatively high temperature. For example, if the softening temperature is from about 100° C. to 140 ° C., the temperature of the heat source will generally be from about 300° C. to 1000 ° C. and the heat source will be positioned from about 0.1 to 50 mm from the tips of the prongs.

After portion P (or P') has been heated, the base 12 moves to conformation station 112, at which time base 12 passes between conformation roll 114 and drive roll 116. Conformation roll 114 forms the portion P (or P') of the prongs into a desired head shape, as will be described in further detail below, while drive roll 116 advances base 12 and flattens it against roll 114 to enhance head uniformity. It is preferred that the temperature of conformation roll 114 (the forming temperature) be lower than the softening temperature. Maintaining the conformation roll 114 at this relatively low temperature has been found to allow the conformation roll to flatten into a desired head shape the spherical ("ball-shaped") tips of prongs that are generally formed during the previous heating step. A low forming temperature also prevents adhesion of the thermoformable polymer to the conformation roll. Generally, to obtain the desired forming temperature it is necessary to chill the conformation roll, e.g., by running cold water through a channel 115 (FIG. 8) in the center of the roll, to counteract heating of the conformation roll by the heat from portion P (or P') of the prongs. If further cooling is needed to obtain the desired forming temperature, the drive roll may be chilled in a similar manner.

In many cases the conformation roll may be a smooth cylindrical roll, and the multi-prong features of the preform member alone, by deforming, provide a desirable complex edge surface for fiber-engaging head portions as illustrated in FIGS. 3–6.

Figure 9:
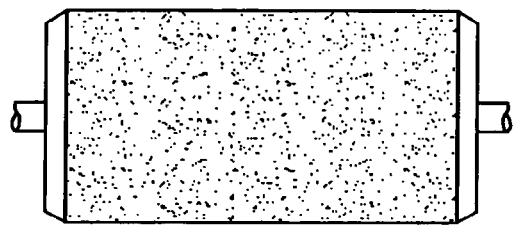
FIGS. 9–13 depict texturizing head-forming rolls.
Figure 10:
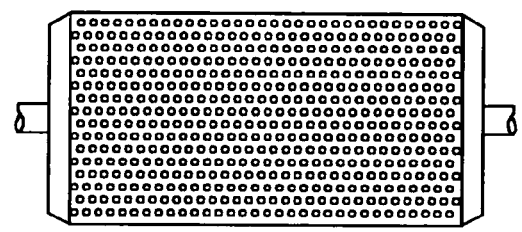
Figure 11:
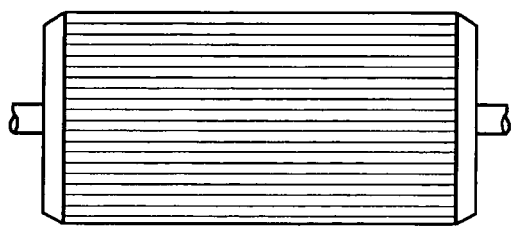
Figure 12:
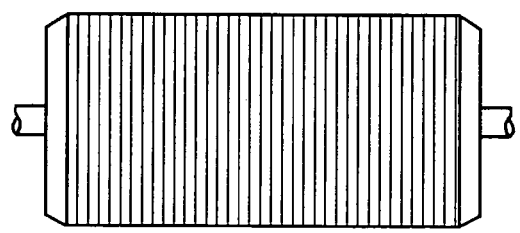
Figure 13:
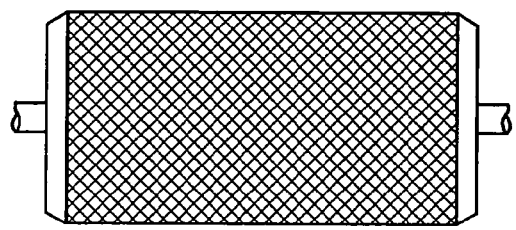

Referring to FIGS. 9–13, however, for other circumstances a surface texture of conformation roll 114 is provided that will determine the shape of the heads that are formed. If disc-shaped heads having a smooth top surface are desired, the surface texture is smooth and flat as previously mentioned. If a sandpaper-like surface is desired, the surface texture of the conformation roll is made sandpaper-like (FIG. 9). If mushroom-shaped (domed) heads are desired, the conformation roll surface is provided with a plurality of substantially hemispherical indentations ("dimples") to form the dome portion of the heads (FIG. 10). Disc-shaped heads having a "wavy" shape can be formed using the conformation roll surfaces shown in FIGS. 11 and 12. The diamond-lattice conformation roll surface shown in FIG. 13 will give the head portions a pyramidal shape.

Preferably, when the surface texture includes dimples, the density of the dimples is substantially uniform over the roll surface, and is substantially greater than the density of the prongs. If the density is equal, improper registration may result in none or few of the prongs being contacted by dimples.

The spacing of the conformation roll 114 from the drive roll 116 is selected to deform portion P (or P') to form the desired head shape, without excessive damage to the unheated portion of the stems. It is also preferred that the spacing be sufficiently small so that the drive roll flattens base 12 and provides substantially uniform contact pressure of prong tips against the conformation roll. Relatively low pressures generates fasteners where the prongs are only partly deformed (see, for example, the fastener of FIGS. 3 and 16), while relatively high pressures generate fasteners in which the prongs are fully deformed (see, for example, the fastener of FIGS. 5 and 15).

Figure 7:
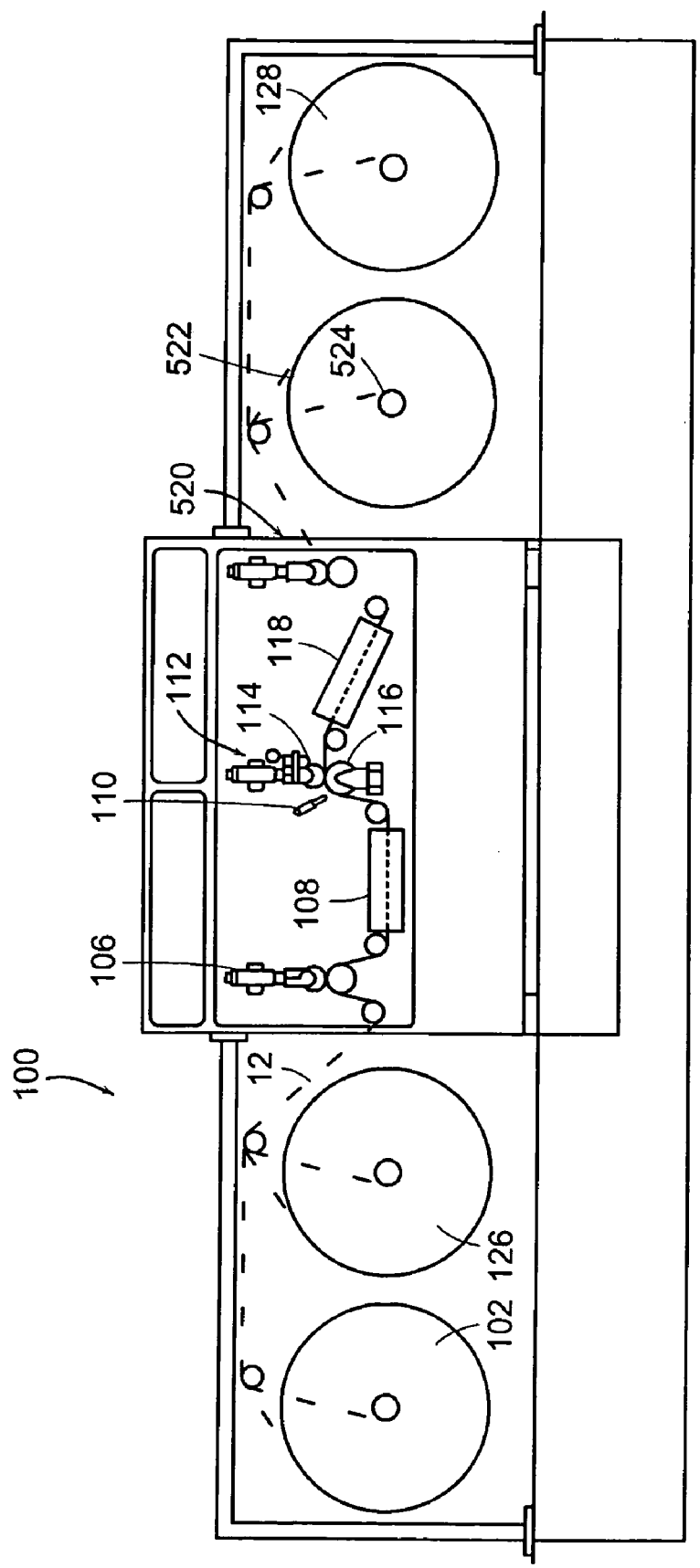
FIG. 7 is a side view of an apparatus for making the fasteners, for example, of FIGS. 3A–6A.

Next, the base 12 moves to a cooling station 118 (FIG. 7). Cooling station 118 cools the formed heads, e.g., by cool air, preventing further deformation of the heads. Preferably, the heads are cooled to approximately room temperature. The cooled base is then moved through driving station 520 and wound onto take-up roll 522 by winding element 524.

Alternate supply and take-up rolls 126, 128 are provided so that when supply roll 102 is depleted and/or when take-up roll 524 is filled, the appropriate roll can be easily replaced without disrupting the process.

Suitable materials for use in forming the fastener are thermoplastic polymers that provide the mechanical properties that are desired for a particular application. Preferred polymers include polypropylenes, such as those available from Montell under the tradename MOPLEN, polyethylene's, ABS, polyamides, and polyesters (e.g., PET).

Other embodiments are of course possible.

The head structures, though derived from simple parallel surface preforms with no overhang of the base, may thus have desired shape that provides a complex surface overhanging the base to an extent sufficient to provide a multi-directional loop engagement having desired strength characteristics.

Moreover, while the process described includes only a single heating of the prongs and a single pass through a conformation station, these steps may be repeated one or more times to provide other head shapes. Subsequent conformation stations may have the same conforming surface as the first conformation head, or may have different surfaces.

One or more of at least six advantages may be obtained in using multi-featured preforms such as those shown in FIG. 2, and in later figures to be described. First, the tooling for straight-sided preforms can be relatively inexpensive because no engageable heads or overhanging features need to machined in the tooling for molding the preforms. Second, the spacing between the prongs or other upwardly extending features enable good heat transfer, as by the convection heat transfer by hot gases in which the features are immersed. This allows for high production rates, and efficient use of capital equipment, space and manpower, hence enabling low cost production. Third, since the headless, upright preforms take up less space than do preforms that have overhanging structures, it is possible to have fastener products that have more engageable heads or knob-like head features per unit area, hence more efficient loop engagement is provided. Discrete, individual engaging head products, (e.g., FIGS. 3) and the variety of coalesced head products (e.g., FIGS. 4, 5 and 6) are each useful under particular circumstances. For example, all of the products of FIGS. 3–6 offer high hook density and good cross-direction engagement. Individual engaging element products (e.g., FIG. 3) are useful when a disposable attachment is required. The multi-prong preform shown in FIG. 18 has different prong heights and enables different engageable element head sizes to be formed on the same stem (best seen in FIG. 19) which with certain useful loop materials increases the probability of engagement, as when loops exist in the material a variety of sizes, as in certain nonwovens. Fourth, since the stem is relatively large, it provides for a good, sturdy support for the small heads so that they can engage a low pile loop material (e.g., a non-woven). Relatively small engaging heads increase the probability for penetration and engagement with small loops when compared with large heads. Fifth, when the small engaging elements are employed, the initial "grab" or seize of an engaging head on a loop can lead to full engagement of that loop. Sixth, the initial "grab" or seize can disturb the bed of loops and bring other loops into range to be engaged by the first head or knob feature or of other heads or knob features on the stem. In other words, the initial engagement of a loop can break up loop interconnections and enable more loops to become exposed. Surprisingly, we have discovered, "engagement breeds engagement." That is to say, that during engagement or during peeling action, the fasteners of the present invention when engaging some loops, expose more loops for engagement by disrupting the loop pile, in a cascade-like effect.

Figure 14:
FIG. 14 is a highly enlarged diagrammatic side view of a low-pile loop material.
Figure 15:
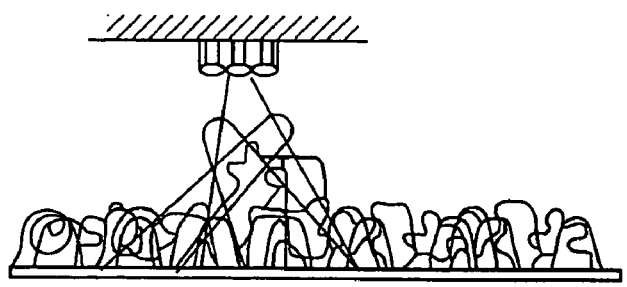
FIG. 15 is a highly enlarged diagrammatic side view of a fully fused hook head of the present invention engaging a low-pile loop material.
Figure 16:
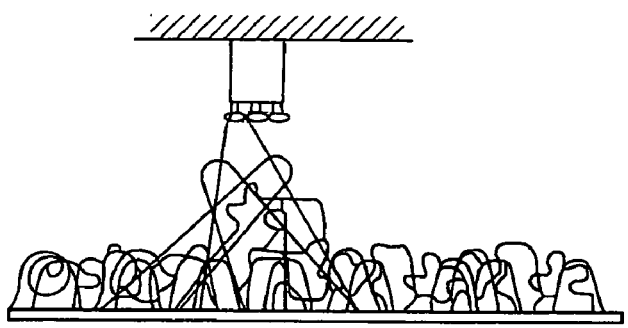
FIG. 16 is a highly enlarged diagrammatic side view of a partially fused hook head of the present invention engaging a low-pile loop material.
Figure 17:
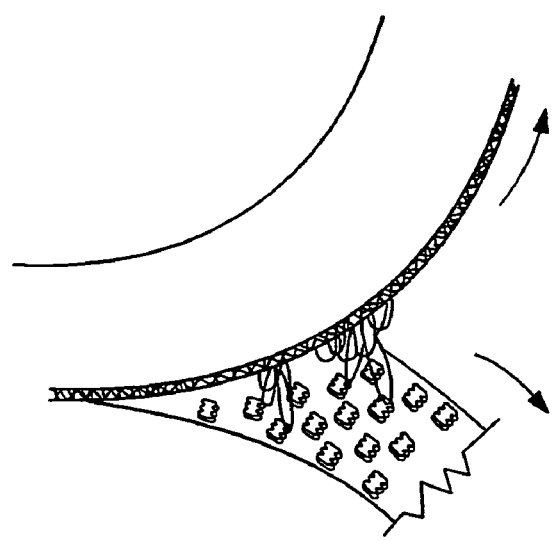
FIG. 17 is a diagrammatic illustration of hook "engagement breeding engagement".

FIG. 14 is a diagrammatic side view of a low-pile loop material that has a variety of loop sizes and a degree of loop entanglement. FIG. 15 illustrates that initial engagement of a hook of the current invention can aid in dis-entanglement of the loops in the low-pile loop material exposing them for engagement by other hooks. FIG. 16 shows the same effect with a fastener only partially fused such as that of FIG. 3. FIG. 17 suggests that during peeling action, the fasteners of the present invention expose more loops for engagement by disrupting the loop pile.

In respect of the range of constructions that are useful employing the principles disclosed refer again to FIG. 2. In FIG. 2, the dimension A represents the overall height of the preform B the prong height, C the spacing between prongs in the cross-machine direction, D the prong thickness in the cross-machine direction, E the spacing between prongs in the machine direction, X is the prong thickness in the machine direction, F the width of the preform stem in the cross machine direction, and G the thickness of the preform stem in the machine direction. The dimensions may range as follows.

|  | General Range | Preferred Range | Most Preferred Products for Personal Care and the like |
|---|---|---|---|
| A = | 0.007 to 0.080 inch | 0.010 to 0.040 inch | 0.013 to 0.030 inch |
| B = | 0.0014 to 0.080 inch | 0.002 to 0.040 inch | 0.003 to 0.010 inch |
| C = | 0.002 to 0.012 inch | 0.002 to 0.010 inch | 0.002 to 0.006 inch |
| D = | 0.002 to 0.020 inch | 0.002 to 0.008 inch | 0.002 to 0.004 inch |
| E = | 0.002 to 0.010 inch | 0.002 to 0.008 inch | 0.002 to 0.004 inch |
| F = | 0.002 to 0.020 inch | 0.002 to 0.012 inch | 0.003 to 0.012 inch |
| G = | 0.002 to 0.020 inch | 0.002 to 0.012 inch | 0.003 to 0.012 inch |
| X = | 0.001 to 0.010 inch | 0.001 to 0.004 inch | 0.001 to 0.004 inch |

FIG. 2A is a plan view of a prong described above with a head, while FIG. 2B is a side view of the prong with its head. The overhang of the head $O_v$ and the head thickness $T_h$ may be expressed in terms of the prong width X:

$O_v \approx 0.3X$ to about $0.7X$; and $T_h \approx 0.5X$ to about $1.3X$.

Preferably, X is from about 0.001 (0.025 mm) to about 0.010 inch (0.25 mm). More preferably, X is less than about 0.008 inch (0.20 mm), and ranges from about 0.001 inch (0.025 mm) to about 0.004 inch (0.10 mm). For a square cross-sectional area such as that shown in FIG. 2, the hook density may advantageously range from 1000–7000 hooks/in$^2$.

Hook fasteners such as these may be useful in personal care products and the like such as diapers, training pants, swim pants, sanitary napkins, panty liners, incontinency garments, and as well, for containers for food storage, covers, filters, towels, paper towels, medical wraps, gowns, surgical drapes, face masks, single patient use devices, packaging closures, outdoor shelters, and other products.

Referring to FIG. 18, again a pattern of six straight, vertical sided prongs extend from a single stem, the central prong 220. In each machine direction row of the preform member is taller than its machine direction neighbors at each side. Referring to FIGS. 19–22, in some implementations, during the flat-topping of the preform shown in FIG. 18, the taller prongs 220 are bent to overhang the base in the cross-machine direction. This may occur because of freedom of interference in that direction in comparison to the other directions in which there are neighboring prongs. Bending outwardly as illustrated, can enable better shear performance and better cross-direction engagement of the engaging heads. One way to create such fastener, for example, is to heat all the prongs as discussed above and then to cool the higher prongs selectively at an appropriate cooling station (not shown). In one example, the heights $H_2$ of the lower prongs are about 0.025 inch and the height $H_1$ of the higher prongs are about 0.030 inch. In another case, the taller stems provide more material for melting down to a deformation limit, resulting in larger head formations and overhang in the central region, as depicted in FIGS. 19–22. This has the desirable omni-directional effect, enabling the fastener to have loop engaging ability regardless of the direction of relative shear movement between a so-formed hook component and a matching loop surface.

Figure 24:
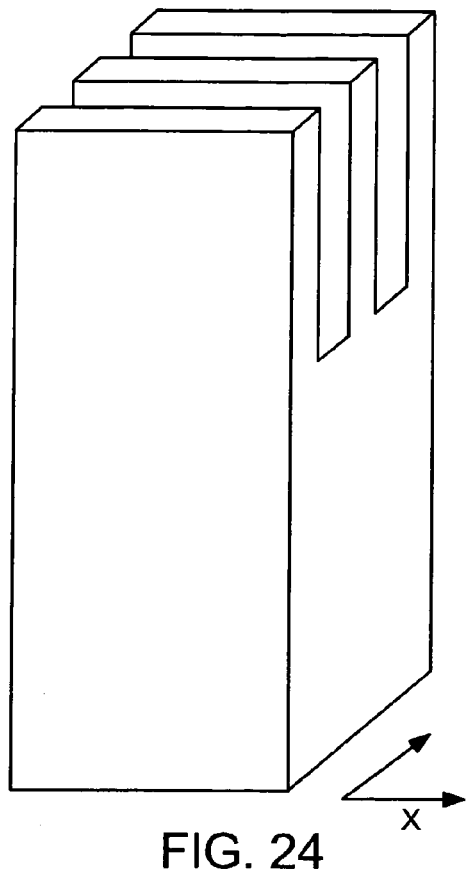
FIG. 24 is a perspective view of a three-prong preform member.
Figure 25:
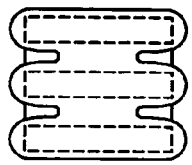
FIGS. 25–27 are respective top views of fastener members made from the preform member of FIG. 24 with varying degrees of head coalescence.
Figure 26:
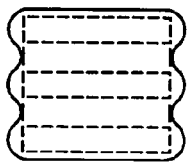
Figure 27:
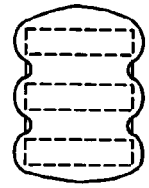

Referring to FIGS. 24–27, a three prong preform is shown along with fastener heads made from the preform of FIG. 24. The prongs, in this instance, for a given overall size, are sturdier, here in the X, cross-machine direction, and provide more material for deformation.

Figure 28:
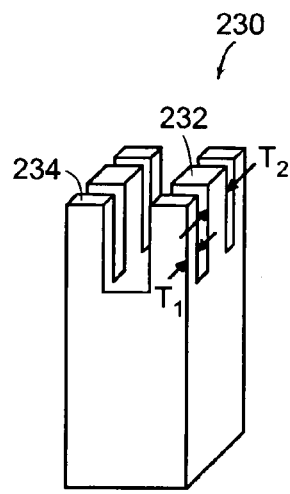
FIG. 28 is a perspective view of a six-prong preform member having prongs with two different machine direction thicknesses.
Figure 29:
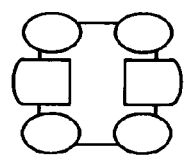
Figure 30:
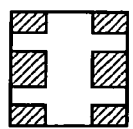
FIG. 30 is a top diagrammatic view of a tooling component for making the preform member of FIG. 28.

Referring to FIG. 28, preform member 230 has six prongs extending upwardly from the stem, as before. In this case, the middle prongs 232 have a greater thickness in a selected direction than do the neighboring prongs 234 on either side. For example, the thickness $T_2$ of the thicker prongs 232 may range between about 0.003 inch to about 0.008 inch, while the thickness of the thinner prongs 234 range about 0.001 inch to about 0.004 inch. This enables forming a range of different engaging head sizes, for example, as shown in FIG. 29, to enable engagement of different loop sizes. FIG. 30 illustrates a portion of the tool that creates the preform of FIG. 28. Methods of forming such tooling will be discussed below, but its simplicity and low cost is evident just from the figure.

Figure 31:
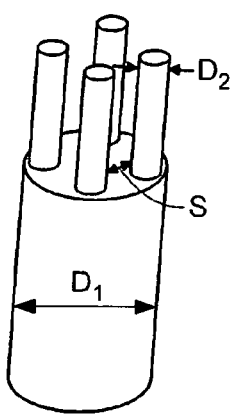
FIG. 31 is a perspective view of a four-prong preform in which both stem and prongs have circular transverse cross-section.
Figure 32:
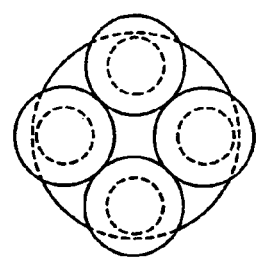
FIG. 32 is a top view of a fastener member made from the preform member of FIG. 31.

In FIGS. 31 and 32, a four-prong preform member and the resulting fastener, respectively are shown. In this case, both the stem and the prongs have circular transverse cross-sections. Tooling for such preform products is made by simple drilling, e.g., by employing EDM or laser drilling. Useful ranges of diameters may be determined from the forgoing table in which $D_1$ corresponds generally to F or G in the table, and $D_2$ and S correspond to dimensions X and E in the table, respectively.

Figure 33B:
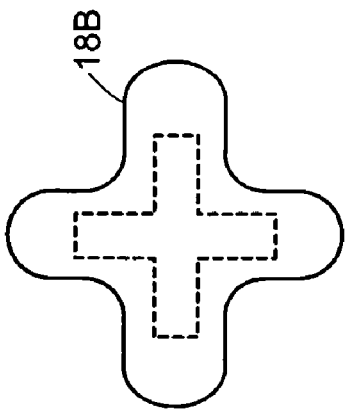
FIGS. 33, 33A and 33B illustrate a quadrolobal M hook while FIGS. 33C, D and E illustrate the molded preform product from which it is fabricated
Figure 33A:
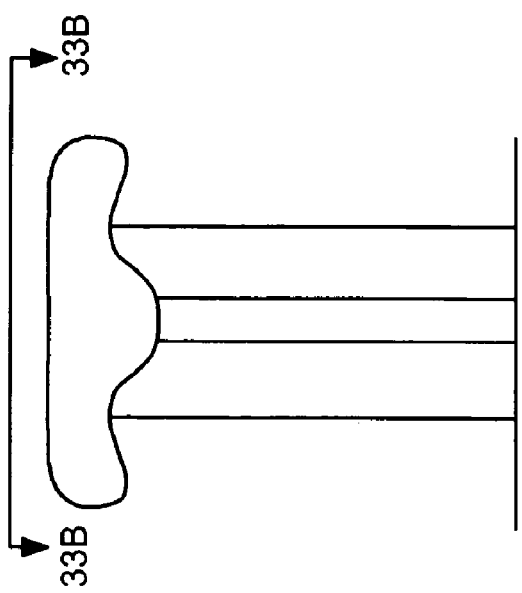
Figure 33:
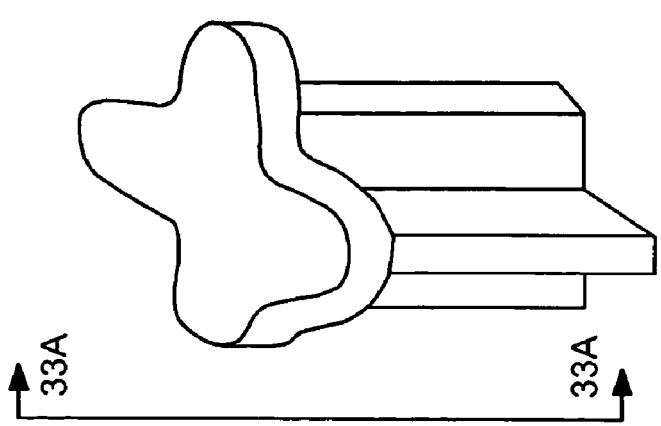
Figure 33F:
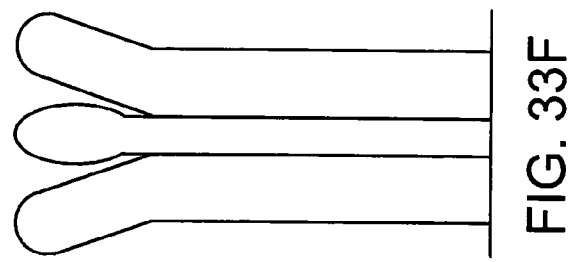
FIG. 33F illustrates the condition of the terminal end of the preform of FIG. 33D after non-contact heating and before flat topping.
Figure 33D:
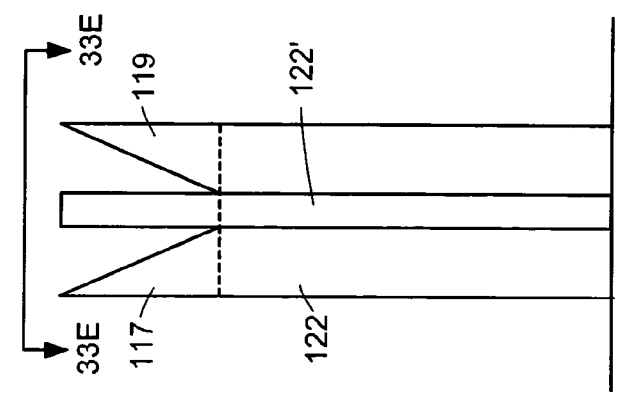
FIGS. 33G, H and I are cross-sectional views that illustrate mold tooling for molding the preform element of FIG. 33.
Figure 33E:
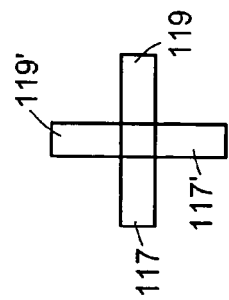
Figure 33C:
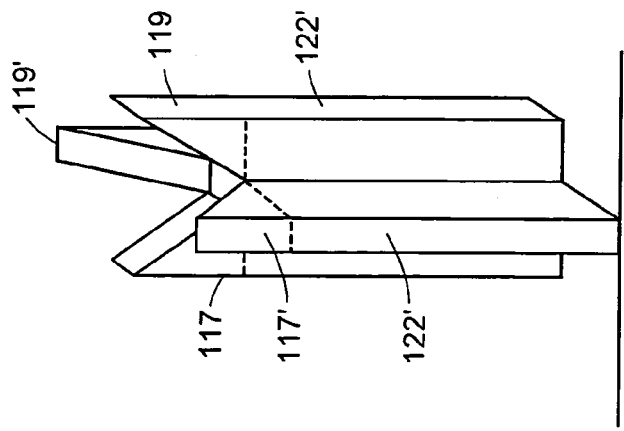
Figure 33G:
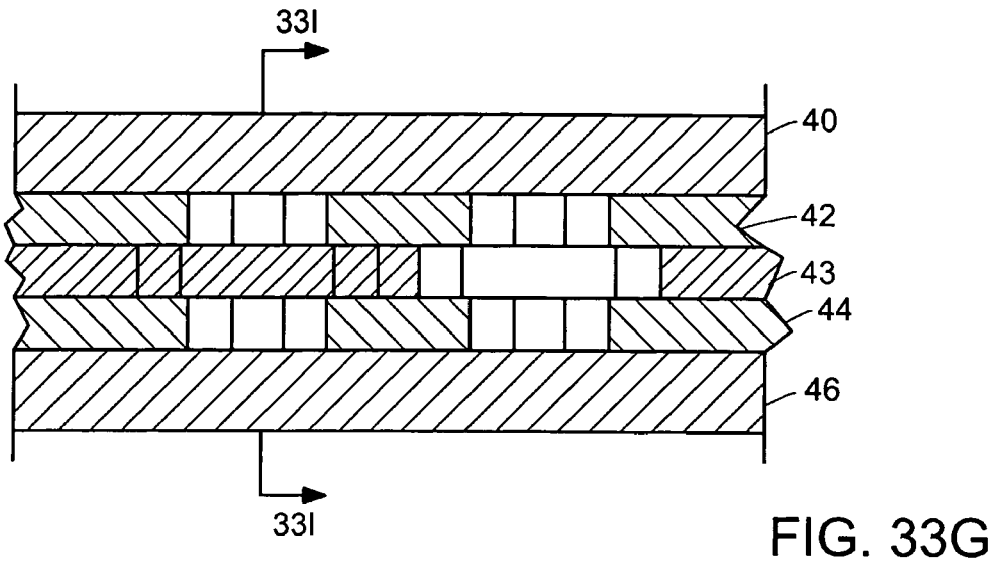
Figure 33H:
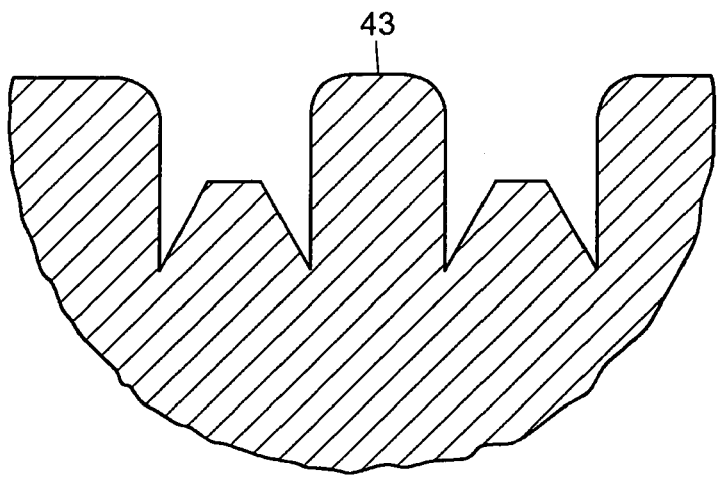
Figure 33I:
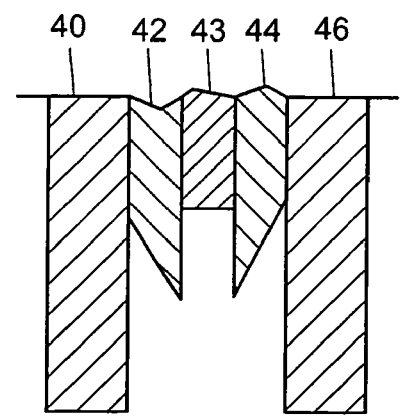

FIGS. 33, 33A and 33B, perspective, side and top views, respectively, show a quadrolobal "M" hook, so-named "M" because of the configuration of the preformed stem profile, shown in corresponding FIGS. 33C, D and E. FIGS. 33 G, H and I illustrate simple mold tooling for the element of FIG. 33C.

Figure 34E:
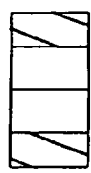
FIGS. 34C, 34D and 34E illustrate the molded preform product from which it is formed, and FIG. 34A' illustrates a hook profile similar to FIG. 34A, but formed in a different manner.
Figure 34B:
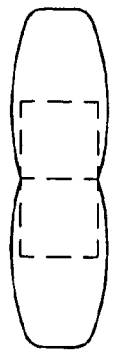
FIGS. 34, 34A and 34B illustrate, in the usual manner, another embodiment, based on a single cross-machine extending, M-shaped preform.
Figure 34D:
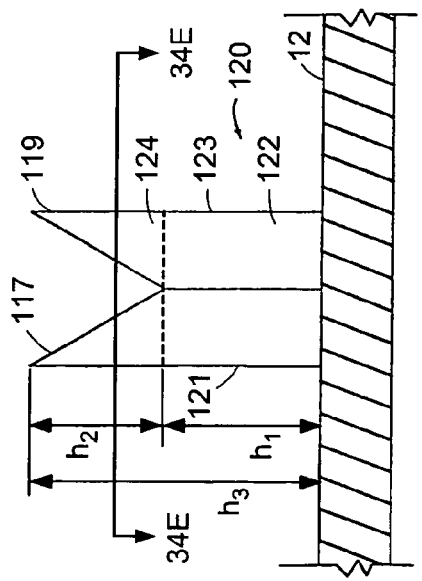
Figure 34A:
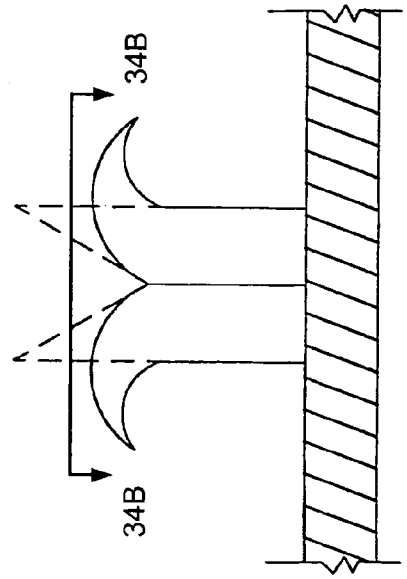
Figure 34:
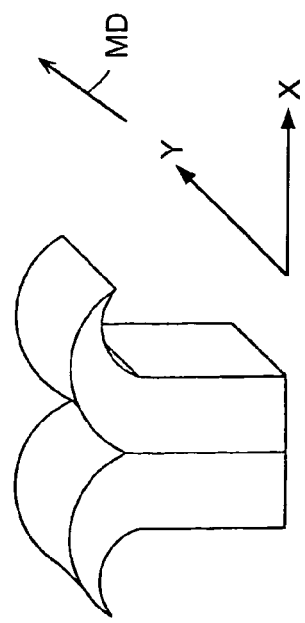
Figure 34C:
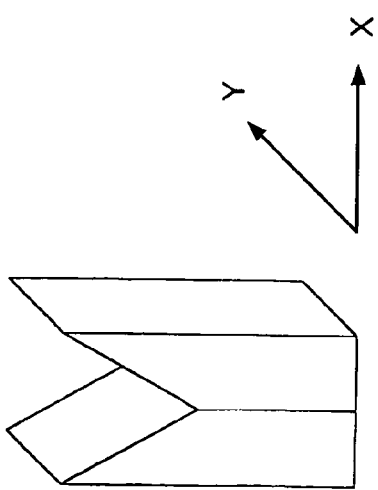
Figure 34A:
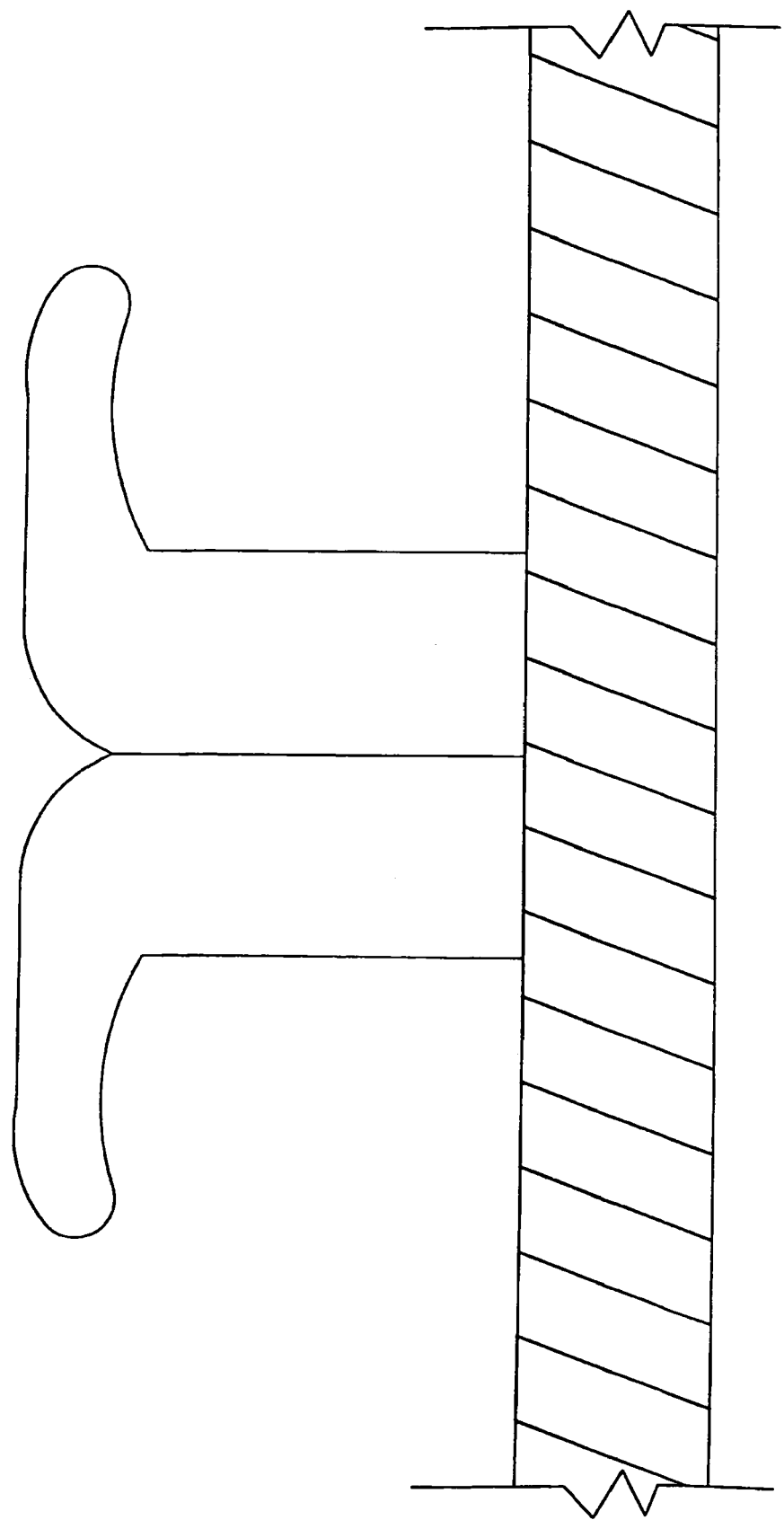

Referring first to FIGS. 34C, D and E, a planar "M" perform, for forming a "bilobal" hook, has more polymer at the outer-most portions of the stem, the amount of polymer decreasing linearly moving toward the center of the hollow V. This particular preform stem shape may be used to provide a final fastener product having engagement characteristics different from the previously described examples. Preform stem 120 has a first stem portion 122 attached to base 12 and a second portion 124 that extends from portion 122 to define the overall height of the formation. The stem portion 122 extends for instance to a height, $h_1$, of the order of 0.019 inches, the second portion 124 has a height, $h_2$, of the order of 0.008 inches, the overall height, $h_3$, of the formation being of the order of 0.027 inches. Second portion 124 has outer wedges 117, 119 or prongs at its left and right surfaces 121, 123 that are of triangular form with base at the transition from stem portion 122 and peak or point at the top or adjacent the respective surface 121, 123. Thus a "V" shaped central opening occurs that is devoid of thermoformable resin.

FIGS. 34C, D and E show the "M" stem preform element, oriented in the cross-machine direction, is conceptually formed of two "half M" configuration stem segments, see the corresponding mold tooling shown in FIGS. 34F through 34J.

The principle of a thin fin is employed, i.e. of thickness of about 0.010 inch (0.25 mm) or less, having more of the resin concentrated at the X direction ends of the fins, i.e. at the prongs, defined adjacent vertical side surfaces of the formation. Depending upon the method and degree of deformation, an oval head or the cross-machine "Figure 8" head of FIG. 34B can be obtained. With the quadrolobal M stem of FIGS. 33 similar deformations can be obtained. In the case of the hook depicted in FIG. 33, non-contact heating provides four lobes of molten resin, concentrated at the periphery, see FIG. 33F. Flat-topping of this resin can then produce the head 18B shown in FIG. 33B. The resin, as it melts, finds the path of least resistance to be predominately at the "precipice" provided at the steep sides of the M. If a "super heating" condition is employed, with resins such as Nylon and high density polyethylene, J-shaped profiles are obtainable at the corners.

It is useful to explain here the term "superheating," and how it may be employed to achieve desirable shapes. In general, the non-contact heating step described, is usefully achieved with gas flame heating. When the gas flow rate and orifice sizes are set, the system has an established range of heating capability that is controlled by the distance of adjustment that is independent of the particular polymer. The heating is readily adjusted to enable flat-topping and stabilization of the forms shaped by the cold forming roll 4. By adjusting the distance of the burner closer to roll 3, more heat than the minimum required for flat-topping can be applied. The system remains within the range of the flat-topping action. In that case, flat-topping is effective to distribute the resin and apply a shape, but a point is reached at which it is readily observed that the emerging forms have not yet frozen in that shape, and further, predictable deformation is observed.

It is realized that benefit can be obtained from this secondary, "self-forming" action, following flat-topping. In one case, by choosing a resin having a low heat deflection temperature, the method is used to form rounded mushrooms. For example, low density polyethylene (LDPE) having a heat deflection temperature of 113 degrees F. can be employed (significantly lower than the heat deflection temperatures of 186 degrees F. and 204 degrees F., of high density polyethylene (HDPE) and polypropylene (PP), respectively).

With a given coolant flow through the cold forming roll 4, after satisfactory flat-topping of the LDPE heads is established with frozen shapes emerging, the heater is brought closer to roll 3, and the line speed slowed to apply excess heat. As heating is increased, gradual change in the final conformation of the flat-topped product is observed. A point is reached in which, in a stable process, rounded mushroom shapes are produced. In this case flat-topping is effective to flatten and spread (distribute) the bulbous molten polymer, and following roll 4, the mass sinks and rounds into mushroom form.

By choice of low deflection temperature resin, e.g. certain polyethylenes, and either by making the fin construction very thin and or subjecting the tip portion to large heat transfer by the proximity or intensity of the flame, a "super heated" condition can be obtained in which useful gravity flow of molten resin occurs after passing by roll 4. This condition can for instance also be obtained by maintaining roll 4 at such temperature that it does no entirely solidify the tip portions.

Contact heating the M-configuration may be employed as well, though potentially at slower speeds. Thus a hot roll (or ultrasound heating techniques) may be employed to obtain head shapes that may, in the case of ultrasound or low level heat forming by a heated roll, be more sharply defined.

In the case of non-contact melting followed by engagement by a conformation roll, e.g. for flat-topping, steps can be taken also to limit resin flow back toward the center of the "V" shaped void. This is suggested by FIGS. 34 and 34A, for instance by limiting the non-contact heating so that only the sharp tips of the M are rendered molten, while the larger cross-sections further down the wedge-form section of the M profile are rendered mechanically deformable but not molten. Following this, flat topping with a chilled roll below the softening temperature or in some cases with a heated roll at or even above the softening temperature, provides useful hooks for some applications.

By the flame heat-cold roll technique, thicker hook tips are attainable, attributable to the non-contacted heated resin that melted and rounded under surface tension prior to the flat topping action.

FIG. 33, the 3-D view of a quadrolobal M hook shows a large outer margin portion of the hook head overhanging the base layer. More polymer on the outer head portion on the fin is created from a perform that has more polymer on the outer portion of the fins.

According to this aspect of the invention, the more the hook heads extend past the stem is beneficial for forming a crook for better engagement, to obtain better holding of loops underneath the hook. A greater distance is then required for the loop to slide off when it is at the top of the stem. When it is at the end of the stem underneath the head, a greater distance is required for the loop to travel around the head of the stem before disengagement hence the loop will be held better.

The FIG. 34B top view of FIG. 34A shows the head of the hook is formed in the cross-machine direction, and that the bulk of the polymer has indeed been pushed out to the side.

In FIGS. 34A and 34B it is shown that a large amount of polymer is pressed out to the side. Loop along the base underneath the hook, by the stem, is at approximately the widest portion of the hook. Therefore, the tendency of the loop to slide off will be very low.

FIG. 34A' illustrates another hook profile that is achievable, similar to that of FIG. 34A.

In FIG. 34G the tool ring shown is cut at a 30 degree angle, so that when one of the rings of these figures is flipped over and two rings are placed together, they provide the center two rings of the mold of FIG. 34F. The rings form a peak together, FIG. 34G. In FIG. 34F two outer spacer rings complete the beginning and end portion of the M profile.

In FIG. 34F, the four different rings are 40, 42, 44 and 46, ring 42 being the one turned over 180 degrees, otherwise being the same as ring 44.

Figure 35E:
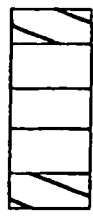
Figure 35B:
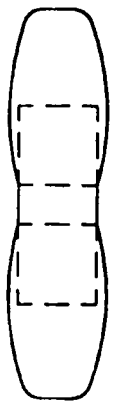
Figure 35D:
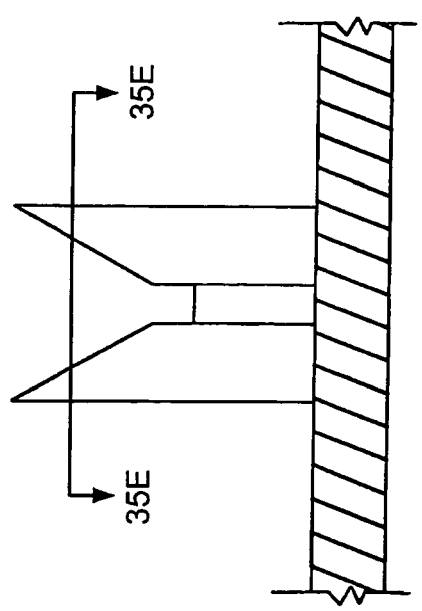
Figure 35A:
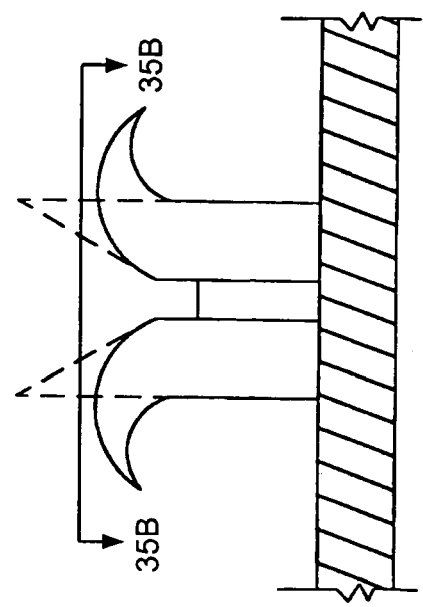
Figure 35:
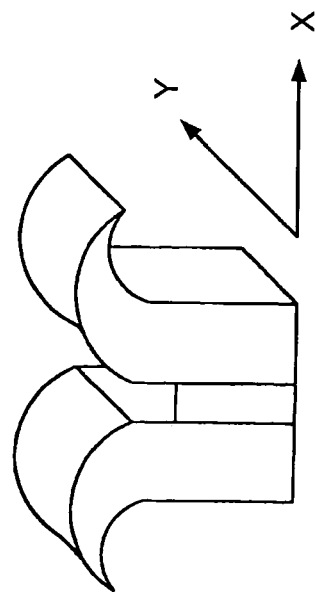
Figure 35C:
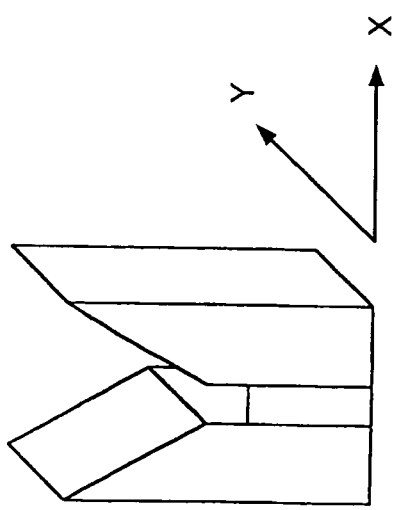
Figure 36:
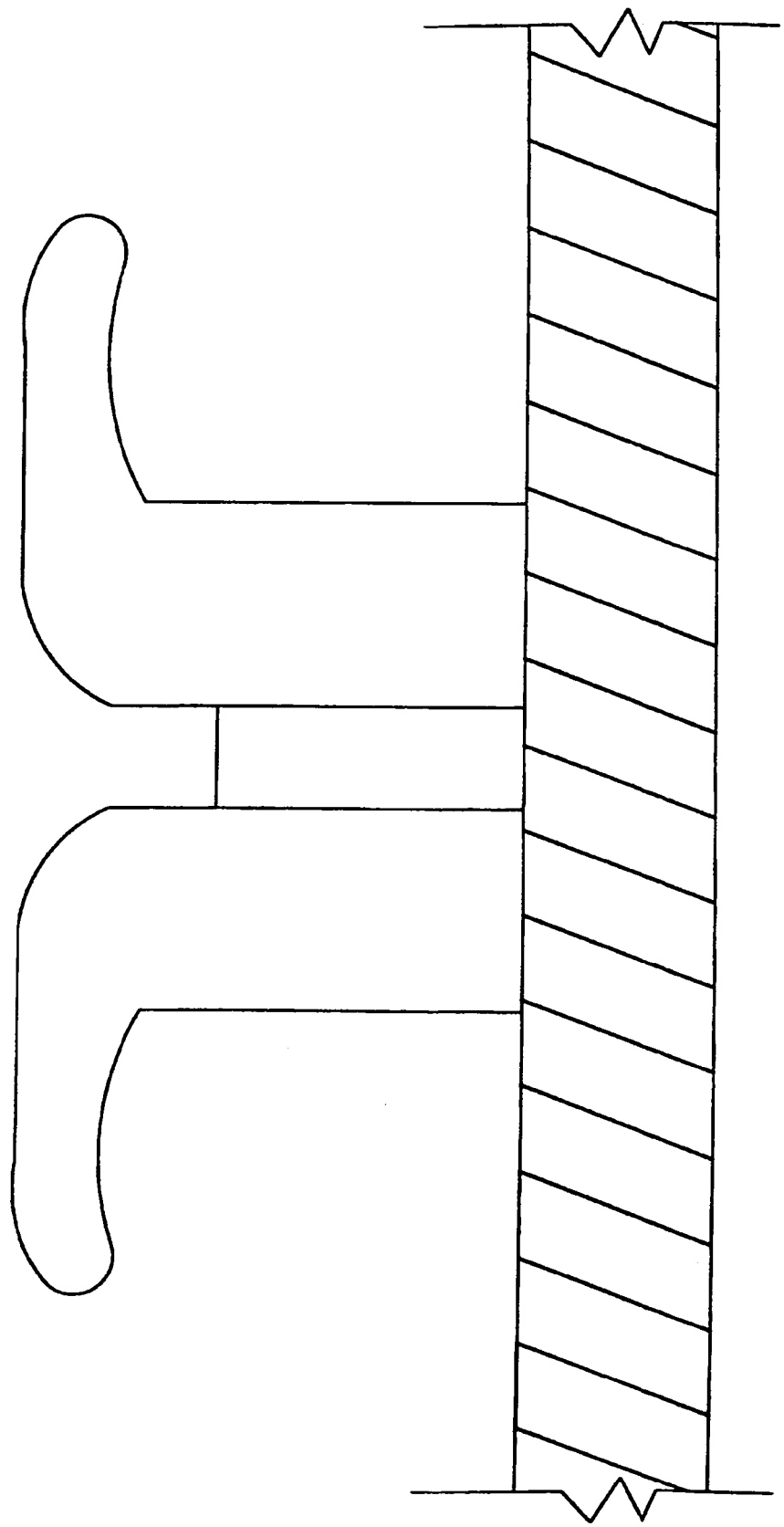
FIG. 36 illustrates a hook profile similar to FIG. 35A but formed in a different manner.

FIG. 35 shows another alternative of the M style hook in which a small rectangular block is placed between the two halves of the M. This design provides a larger cross-directional hook. Referring to FIG. 35A it allows more volume of polymer to be excluded between the two hooks. When this preform formation is flat topped, even more resin is pushed out to the sides. FIG. 36 illustrates a hook profile similar to FIG. 35A but formed in a different manner.

In the example of FIGS. 33 and 34, the stem formations may have an overall height A from base surface to prong tip, a width F, a length X and a prong height B. In one example, F and X are equal to 0.008 inch, A is 0.027 inch and the height B of the prong is about 0.010 inch (0.025 mm).

Figure 37:
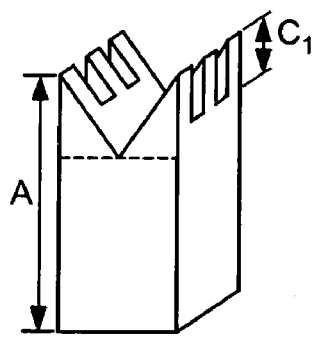
FIGS. 37–38 are perspective views of six-prong, straight-sided M style preform members.
Figure 38:
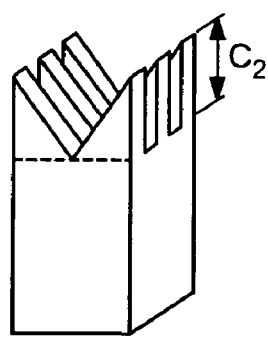

FIGS. 37 and 38 show a preform similar to that shown in FIG. 34C, but trifurcated, to provide six prongs per preform. The depth of the open spaces between the prongs is shown greater in FIG. 38 than in FIG. 37. Relative to the structure shown in FIG. 34C, the structures shown in FIGS. 37 and 38 enable forming smaller engageable head features and better cross-direction engagement. Referring to FIG. 37, the overall height A, for example, is about 0.025 inch and the cutout height C1 is, for example, about 0.005 inch. Referring to FIG. 38, the cutout height C2, for example, is about 0.009 inch.

Figure 39:
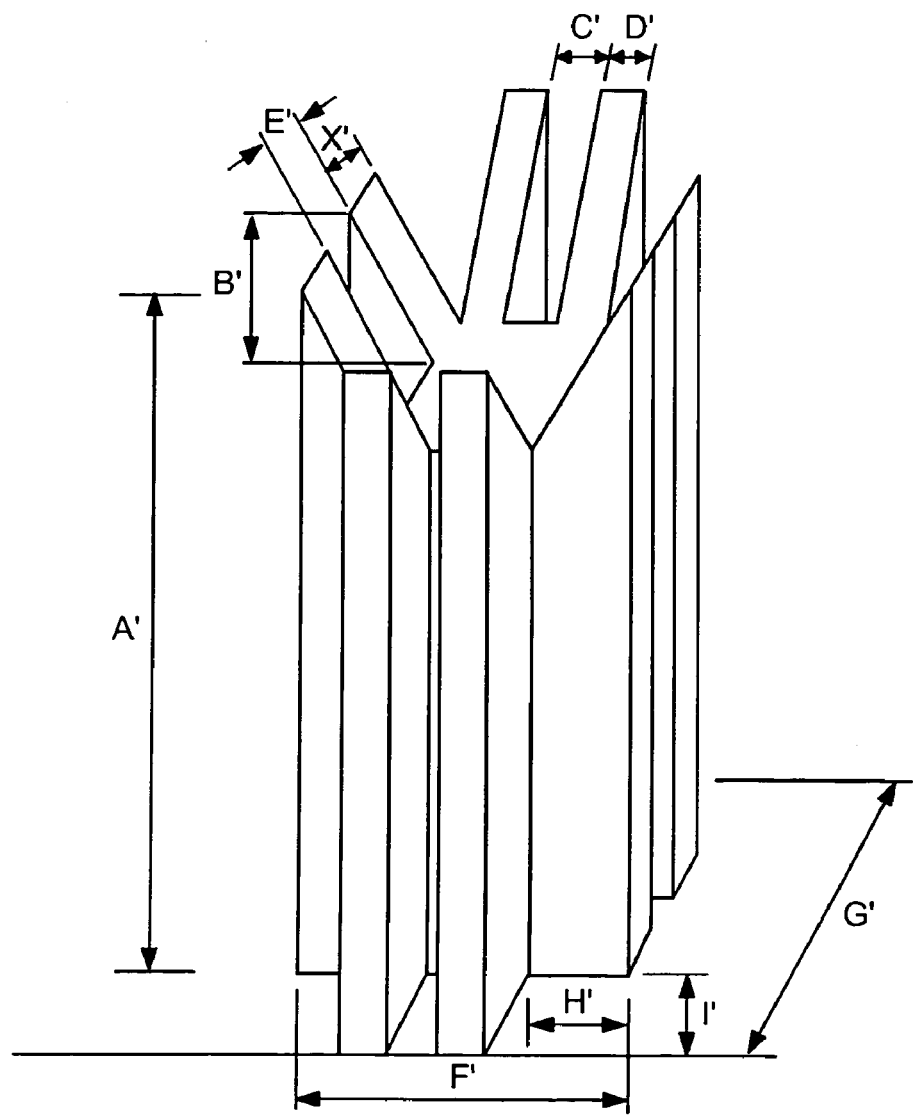
FIGS. 39 and 40 are perspective views of an eight-prong preform member and corresponding fastener member, respectively.

The bifurcated quadlobal M perform of FIG. 39 is to be contrasted with the M quadlobal of FIG. 33. FIG. 33, a perspective view, shows a four-pronged "M" hook, so-named because of the configuration of the preformed stem from which it is formed, appears as the equivalent of crossed M structures. In one example, the lateral extent of each fin is about 0.007 inch, while the overall preform height A is about 0.030 inch.

Figure 40:
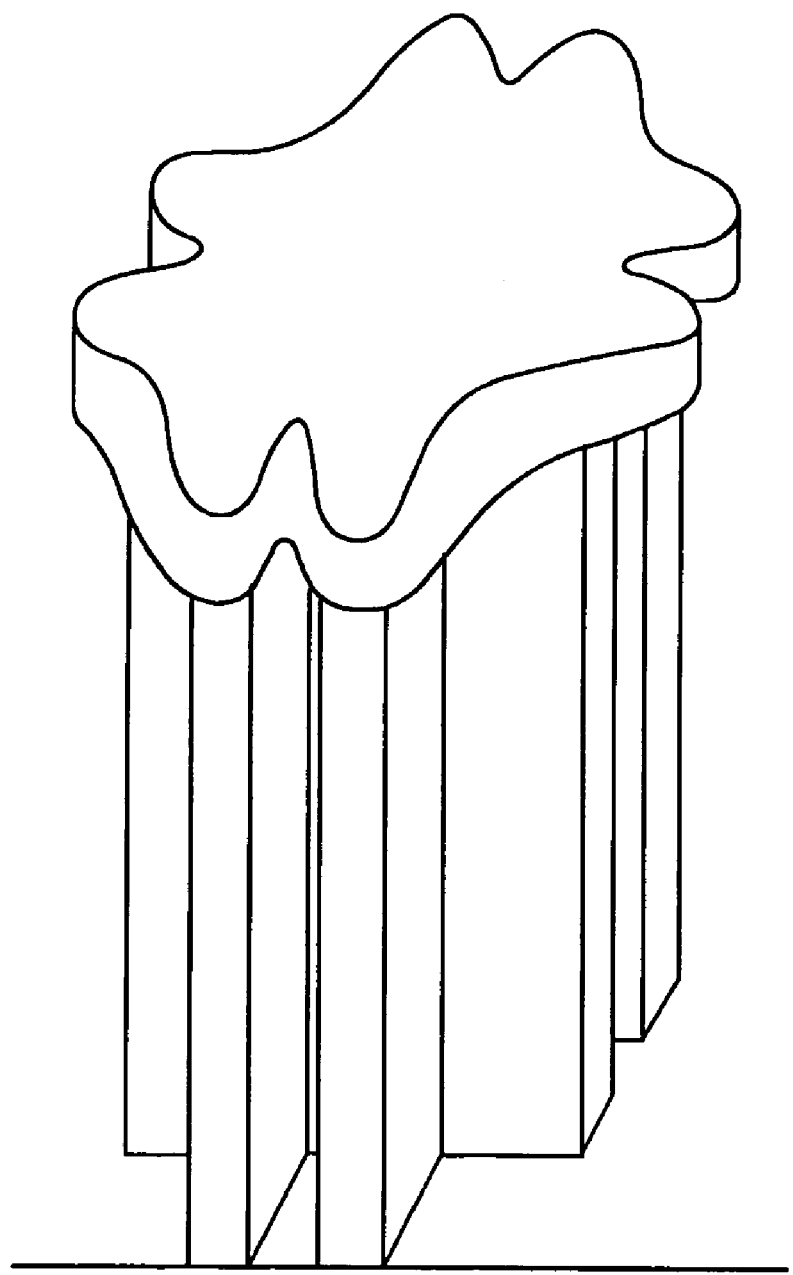

FIG. 39 is similar to the preform of FIG. 33C, except each prong is longitudinally split or bifurcated along its entire length. The resultant flat-topped loop engageable fastener is shown in FIG. 40. The head of this fastener has a desirable, more complex edge than that of the fastener of FIG. 33, enabling more engageable head features to be present per unit area and also enables engagement with very small loops. Referring to FIG. 39, for example, the dimensions may generally range as follows:

|      | General Range      | Preferred Range    | Most Preferred     |
| ---- | ------------------ | ------------------ | ------------------ |
| A' = | 0.007 to 0.080 inch | 0.010 to 0.040 inch | 0.013 to 0.030 inch |
| B' = | 0.003 to 0.027 inch | 0.004 to 0.015 inch | 0.004 to 0.010 inch |
| C' = | 0.002 to 0.012 inch | 0.001 to 0.008 inch | 0.002 to 0.004 inch |
| D' = | 0.001 to 0.020 inch | 0.002 to 0.008 inch | 0.001 to 0.004 inch |
| E' = | 0.002 to 0.012 inch | 0.002 to 0.008 inch | 0.001 to 0.004 inch |
| F' = | 0.007 to 0.030 inch | 0.007 to 0.022 inch | 0.007 to 0.016 inch |
| G' = | 0.007 to 0.020 inch | 0.007 to 0.022 inch | 0.007 to 0.016 inch |
| X' = | 0.001 to 0.010 inch | 0.001 to 0.008 inch | 0.001 to 0.004 inch |
| H' = | 0.002 to 0.012 inch | 0.002 to 0.008 inch | 0.002 to 0.005 inch |
| I' = | 0.002 to 0.012 inch | 0.002 to 0.008 inch | 0.002 to 0.005 inch |

FIG. 41, a highly magnified perspective view, shows a quadrolobal hook created by heating and pressure-heading a stem comprised of thin crossed fin features, fin 21 extending along the cross-machine X axis and thin fin 19 extending along the machine direction, Y axis. These fins have been heated and reformed at their outer extremities to form hook head 18.

Figure 42A:
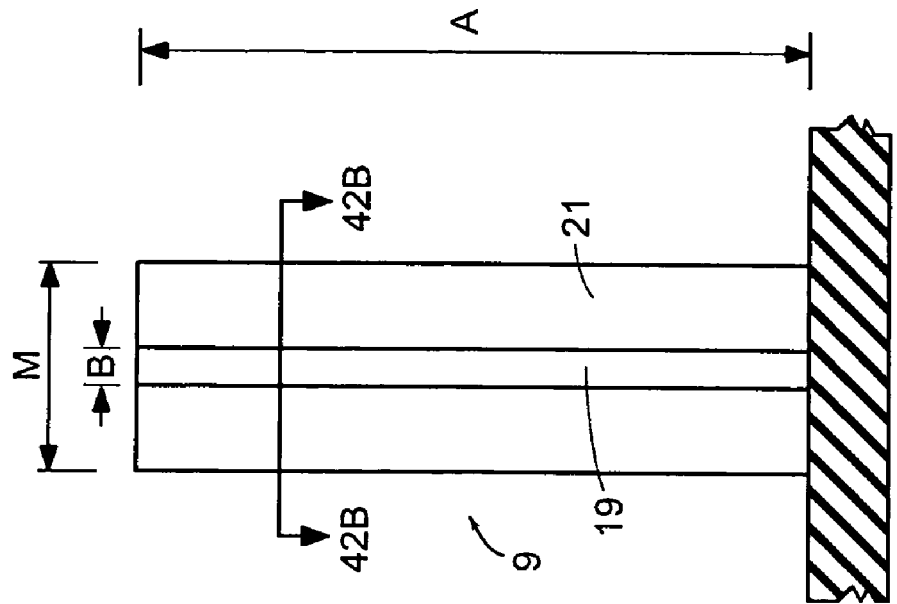
Figure 42:
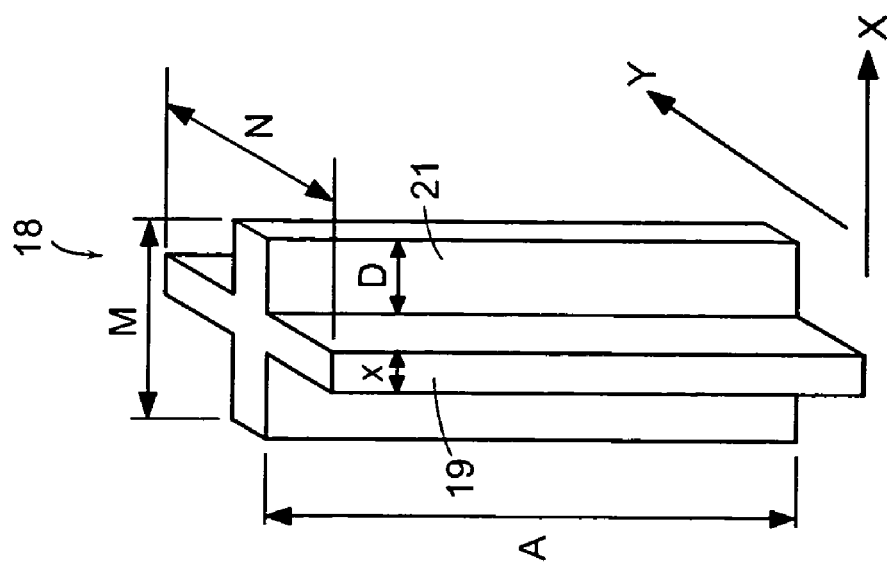
Figure 42B:
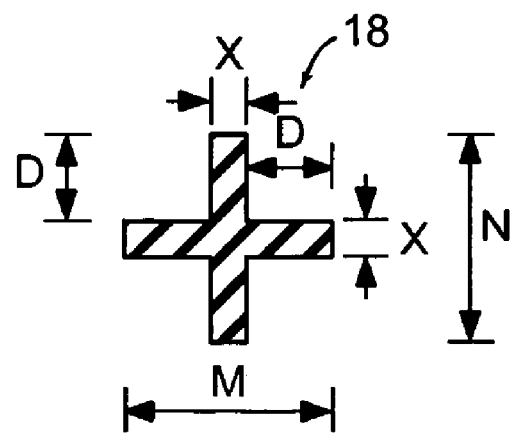

As shown in FIGS. 42 and 42B the stem is of a "plus sign" cross-section profile, fins 21,19 extending symmetrically along the X and Y axes in both directions from a common intersection. The fins have the same along the D the same thickness X and the same height A prior to pressure-heading.

The fin profile ratio is D/X.

The concept of this hook preform element is that with a fin ratio of greater than about 2, preferably around 2½, an improved head overhang is obtainable at the end regions of the fins.

With the stem preform of FIG. 42, such overhangs are provided in each sense in orthogonal directions.

Figure 43:
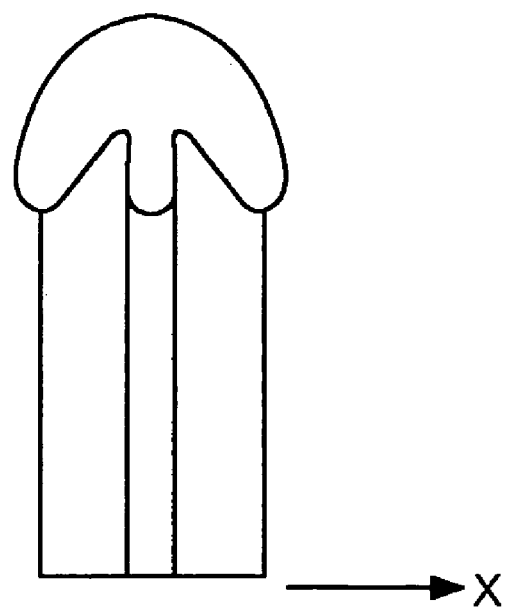
FIG. 43 is a side view similar to FIG. 41A of the stem after it has passed by non-contact heat source, before reaching the conforming roll.
Figure 45:
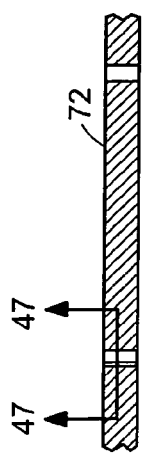
FIGS. 44–49 are views showing tooling for making the preform member of FIG. 42, FIGS. 44 and 45 being partial cross sections on magnified scale taken parallel to the periphery of mating tool rings, FIGS. 46 and 47 being cross section views of greater magnification taken on lines 46–46 and 47–47 respectively on FIGS. 44 and 45.
Figure 47:
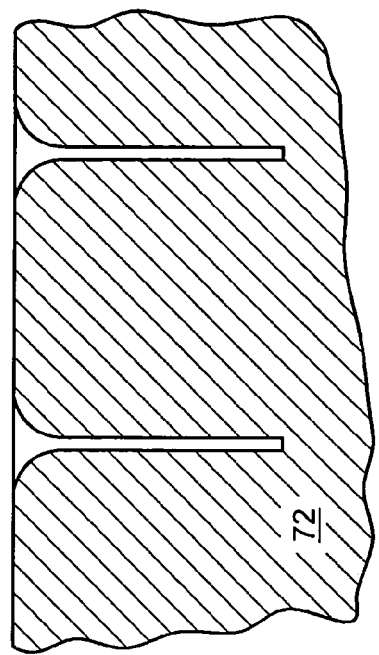
Figure 48:
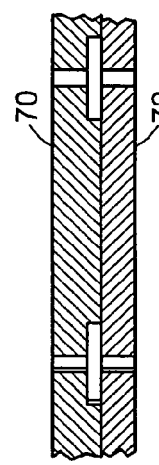
Figure 44:
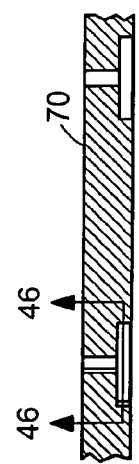
Figure 46:
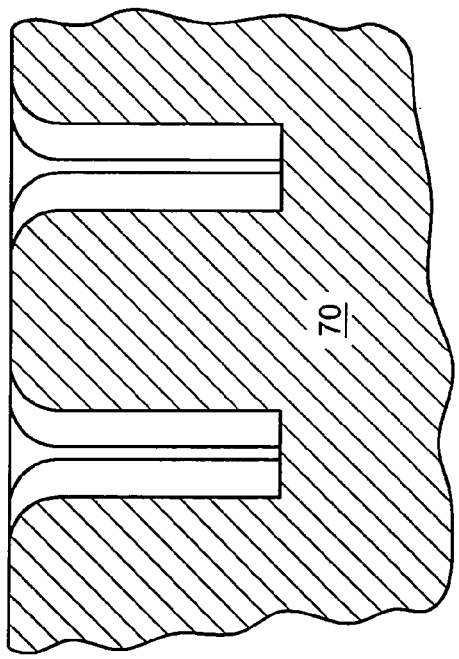

According to this aspect of the invention, a ratio of less than about 2 is seen generally to result in a stem that, when heated and pressure-headed, a head of approximately the shape of a circle centered on the center of the stem results. With a fin ratio of about 2, preferably between 2 and 4, most preferably between about 2½ and 3, the geometry differs significantly from a square or circular cross-section stem such that when heated, surface tension of unoriented polymer will form lobes on the ends of the fins that remain somewhat independent, see FIG. 43, this being especially the case when non-contact heating is employed, with immersion of the side surfaces in the hot convection gases, down to the end of the dashed lines in FIG. 41A.

Referring to FIG. 42, dimension M denotes the stem width in the X axis and N the width in the Y axis, A denotes the overall height, X denotes the thickness of a thin fin and D denotes the lateral extension of each fin from its juncture with its neighbor. For example, the dimensions may generally range as follows:

|  | Preferred Range | Most Preferred Range |
|---|---|---|
| M = | 0.007 to 0.018 inch | 0.008 to 0.015 inch |
| N = | 0.007 to 0.018 inch | 0.008 to 0.015 inch |
| A = | 0.008 to 0.035 inch | 0.013 to 0.027 inch |
| X = | 0.001 to 0.006 inch | 0.001 to 0.004 inch |
| D = | 0.002 to 0.010 inch | 0.003 to 0.008 inch |

Whereas, in general, the extent of non-contact heating is preferably from about 15 to 25% of the total length of the protruding formation, in the special case of convective heating with gases that, from flame combustion, can be about 1000° C., the percentage length heated extends to 30% with good results obtainable.

Figure 49:
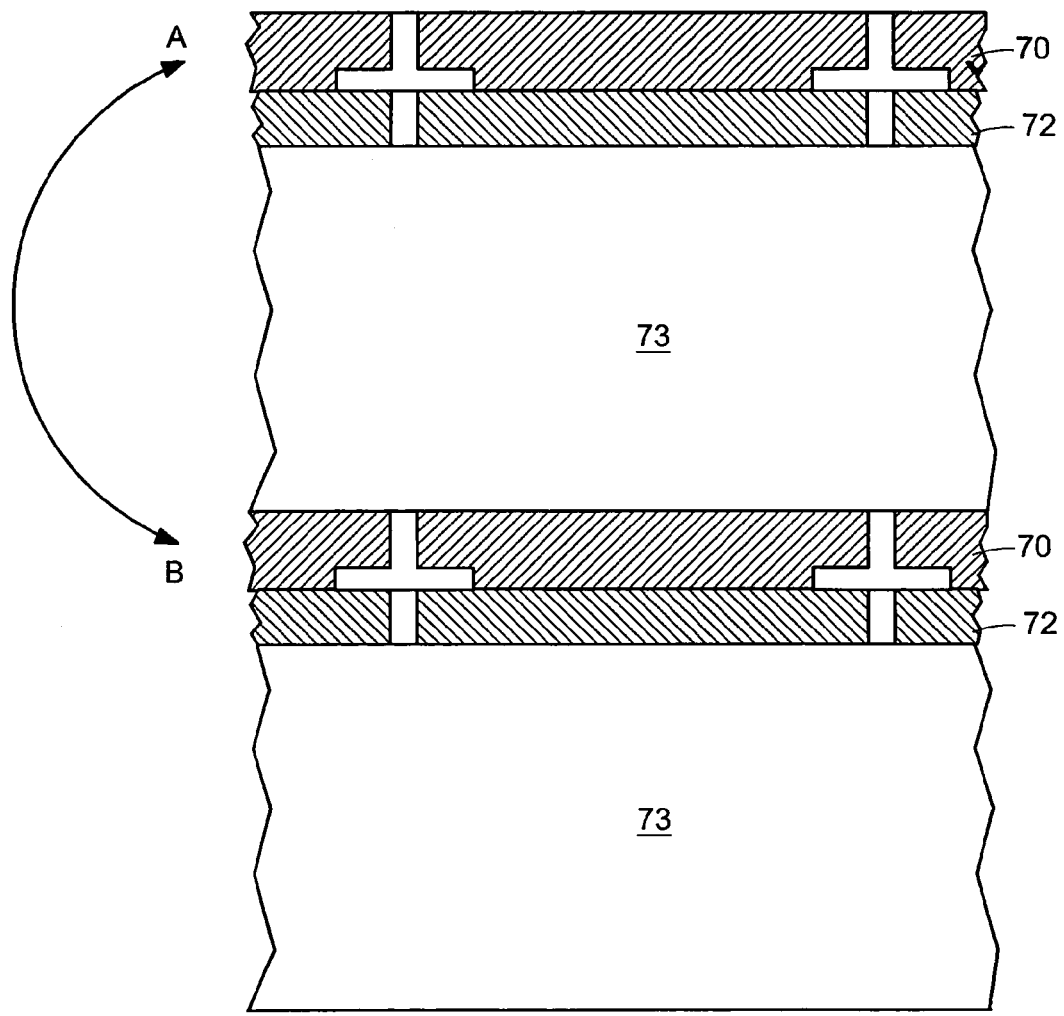

The mold cavities in the mold roll are shown in FIGS. 44–49. Rings 70 and 72 are placed face-to-face together in registry such that when viewed from a plan view down upon the periphery of the mold ring pair, a plus sign mold shape is provided, with fin shaped cavities of between about 2 and 3 length to thickness ratio in accordance with the provided explanation. Many sets of rings are placed side-by-side and pressed onto a shaft, providing an axial distribution of peripheral rows of cavities, FIG. 49. The size of the cavities and their distribution is selected according to the needs of the particular fastening system being constructed. Typically a slight draft angle, e.g. of 1° is employed to enable the molded fin to readily leave its mold. As shown in FIG. 49, solid spacer rings 73 having no mold cavities are placed between pairs of rings 70, 72. A first set of rings 70, 72 is spaced by a spacer ring from the next set, and so on. In the mold pattern of FIG. 49 the mold cavities of adjacent pairs are aligned axially of the mold roll.

In another set-up, an off-set pattern is employed. Adjacent pairs of rings are off-set by 50%, as one useful pattern for enabling engagement with loops.

According to the concept of this embodiment, the plus sign cross-section stems 18 with thin fins 19, 21, when pressure-formed by conformation roll 4, will provide polymer flow in directions of the four lobes off the ends of the fins. For diaper applications, for instance, where cross-machine directionality of the hook is often important due to the orientation of the machine direction of the fastener in the diaper forming process, this can achieve better engagement with the nonwoven loop component of a diaper than by hooks formed with a round or square profile cross-section design.

Figure 51:
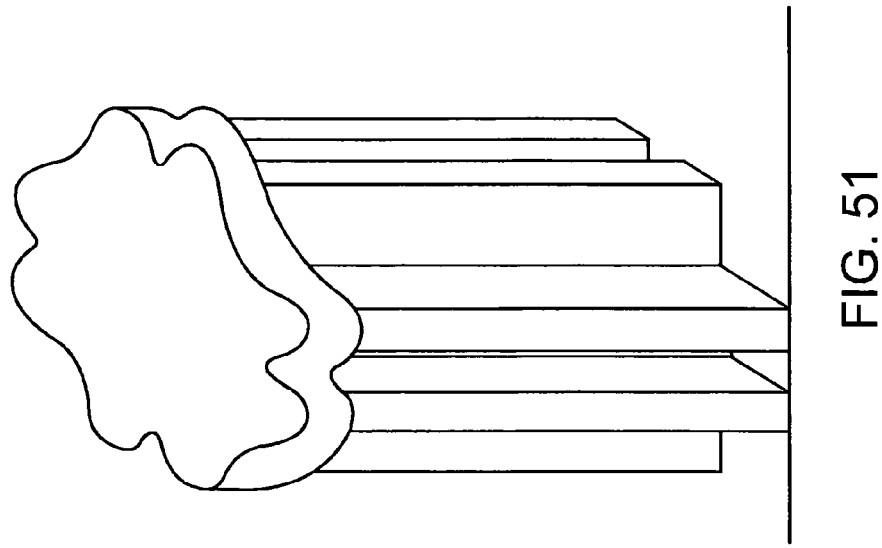
FIGS. 50 and 51, respectively, are perspective views of an eight-feature preform and a fastener member made therefrom.
Figure 50:
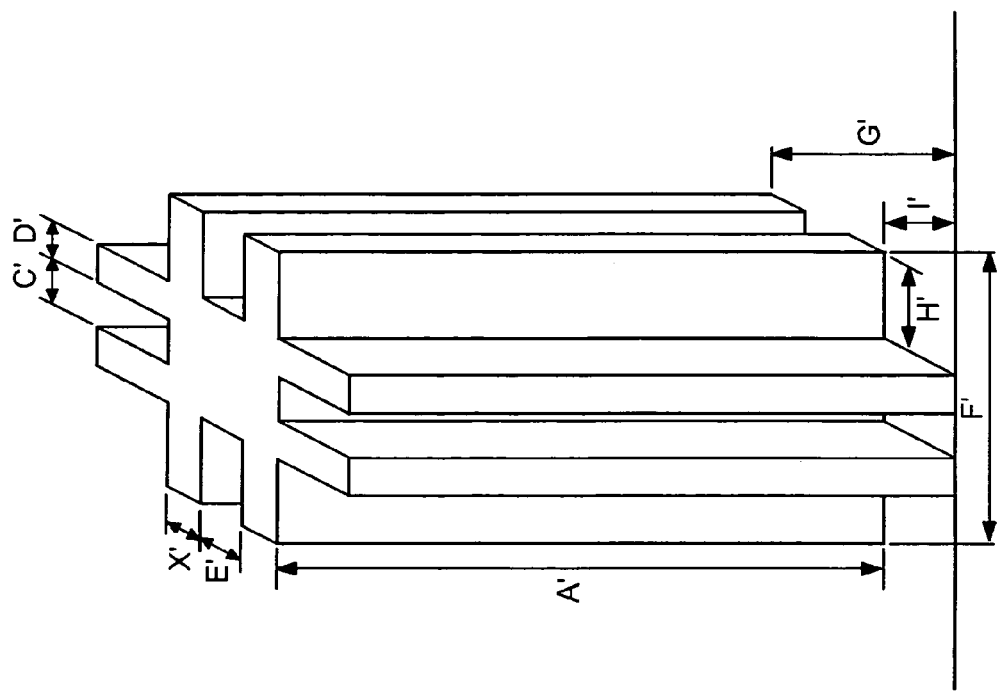
Figure 57:
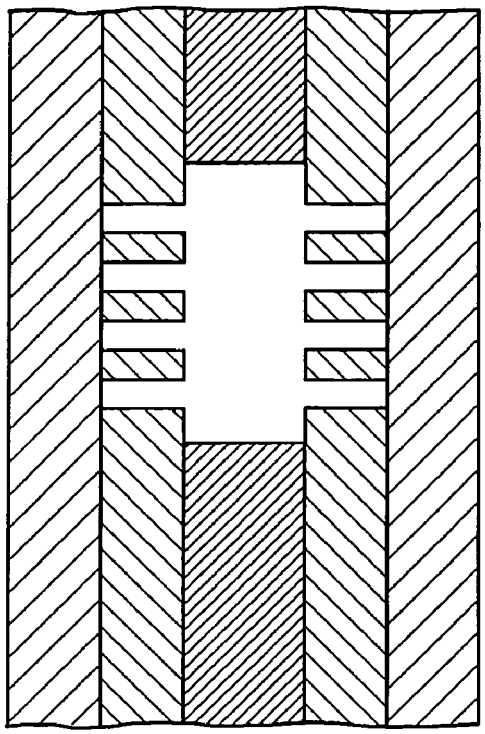
FIGS. 56 and 57, respectively, are top views of an eight-feature fastener member fastener and tooling for its preform.

FIG. 50 shows a preform similar to that shown in FIG. 42, except each prong is divided into portions, i.e., bifurcated. When flat-topped and made loop-engageable (FIG. 51), this fastener enables formation of smaller engageable heads when compared to that shown in FIG. 42. This enables achievement of more engageable elements per unit area and also enables engagement of very small loops. For a square cross-section, the hook density ranges from about 500 to about 2000 hooks/in2. For example, preferred dimensions are as follows:

|  | Preferred Range | Most Preferred |
|---|---|---|
| A' = | 0.010 to 0.040 inch | 0.013 to 0.030 inch |
| C' = | 0.002 to 0.010 inch | 0.001 to 0.004 inch |
| D' = | 0.002 to 0.008 inch | 0.001 to 0.003 inch |
| E' = | 0.002 to 0.008 inch | 0.001 to 0.004 inch |

-continued

|  | Preferred Range | Most Preferred |
|---|---|---|
| F' = | 0.007 to 0.022 inch | 0.007 to 0.016 inch |
| G' = | 0.007 to 0.022 inch | 0.007 to 0.016 inch |
| X' = | 0.001 to 0.008 inch | 0.001 to 0.004 inch |
| H' = | 0.001 to 0.008 inch | 0.002 to 0.005 inch |
| I' = | 0.001 to 0.008 inch | 0.002 to 0.005 inch |

Figure 56:
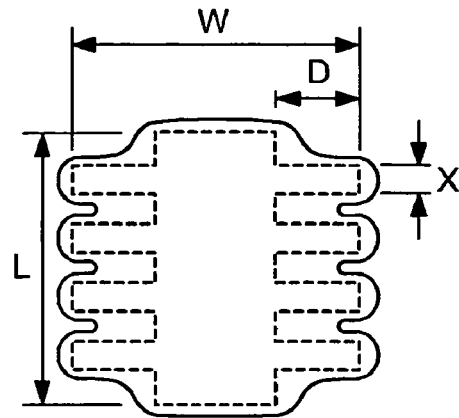

FIGS. 52–57 show a variety of multi-featured preforms, the corresponding fasteners after flat-topping and the tooling that may be used to form the preforms. All of these fasteners have small engaging heads that are highly engaging in the cross-machine direction. Referring to FIG. 56, L, the overall lateral length of the perform, in the machine direction is, for example, about 0.009 inch to about 0.020 inch and W, the overall dimension in the cross-machine direction is for example, about 0.008 inch to about 0.016 inch.

Figure 58:
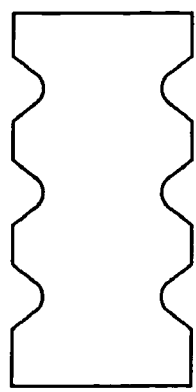
FIGS. 58 and 59, respectively, are top views of an eight-feature preform member and tooling therefor.
Figure 59:
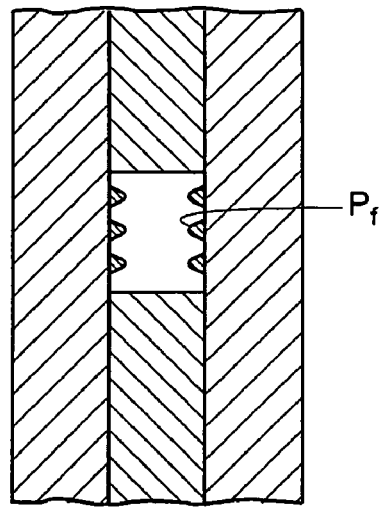

Another technique that may be used to create pronged preforms such as that shown in FIG. 56 or FIG. 58 employs addition of material to preformed tool rings. This method begins by using flat stock tool rings having simple cavities such as, but not limit to, rectangular cavities formed e.g., by laser cutting through the thickness of the flat stock. Tool rings with positive feature, $P_f$ (i.e. added features) such as that shown in FIG. 59, are then placed face-to-face with these flat rings. The flat surfaces of the rings and flat tool rings lay face-to-face against one another, with the positive features $P_f$ of these rings extend into the cavities of the flat tool rings, as shown in FIG. 59. This technique is beneficial for creating preforms with cross-machine direction features as well as j-style and palm tree hooks facing in the cross-machine directions. Tool rings such as these may be built up with a high degree of accuracy because only the highly accurately mating faces come into contact.

Figure 60:
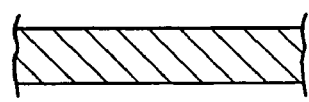
FIGS. 60–65 comprise a sequence of views illustrating steps in the making of the tooling of FIG. 59.
Figure 61:
Figure 62:
Figure 63:
Figure 64:
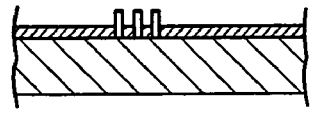
Figure 65:
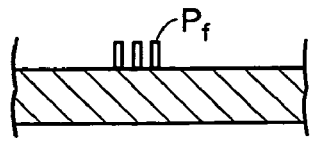

The features on the tool rings may be created by various techniques including electroplating, stamping, etching, milling, EDM, etc. The electroplating option is shown in FIGS. 60–65. The flat stock tool ring, FIG. 60, is first coated with a photo resist layer, FIG. 61. A mask is placed on the resist layer, FIG. 62, and is UV exposed. Exposed areas of resist are then removed leaving the tool ring exposed in these areas, FIG. 63. Metal is then preferentially electroplated in these exposed areas, FIG. 64. The resist is then removed leaving the tool ring as seen in FIG. 65. This is one illustration of the electroplating process, it is understood there are other techniques that create similar features.

Figure 66:
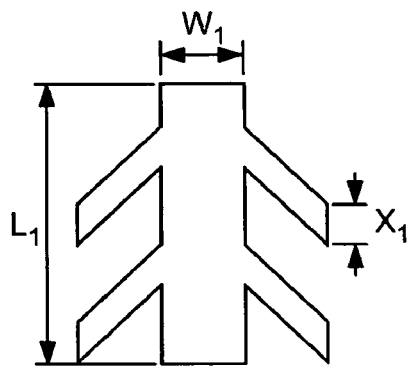
FIGS. 66 and 67, respectively, are top views of a four-feature preform member and tooling therefor.
Figure 67:
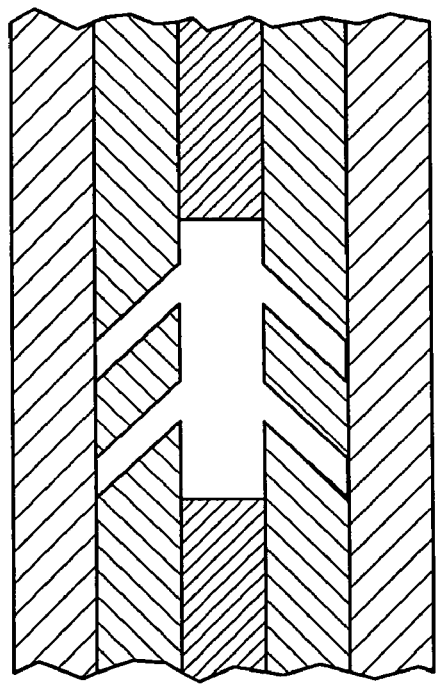
Figure 68:
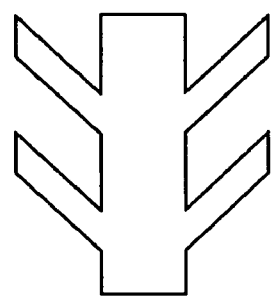

FIGS. 66, 68–72 are alternative, multi-direction, multi-pronged preforms, while FIG. 67 illustrates tooling for the preform of FIG. 66. When the corresponding fasteners are formed from these preforms, the fasteners provide multi-directional engagement from a single stem. The dimensions of $L_1$, $W_1$ and $X_1$ can be, for example, about 0.010 inch to about 0.020 inch, about 0.004 inch to about 0.009 inch, and about 0.001 inch to about 0.005 inch, respectively. FIG. 73 is a top view of a fastener formed from the preform of FIG. 72. These have in common thin fin constructions the ends of which form vertical features about which fibers engage. FIG. 67 illustrates the simple tooling by which diagonally extending thin fins can be created, to provide both cross machine and machine direction effects.

Figure 74:
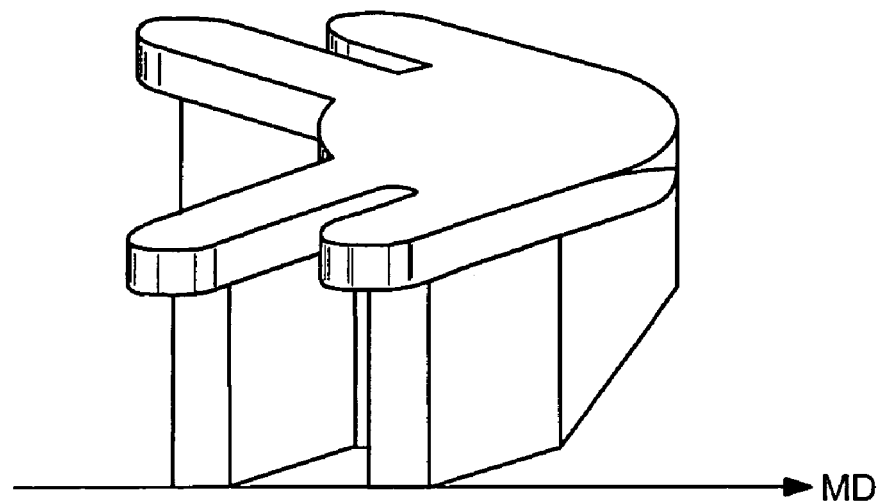
FIGS. 74 and 75 are perspective views of multi-feature fastener members formed with fin elements lying at an acute angle to the machine and cross machine directions.
Figure 75:
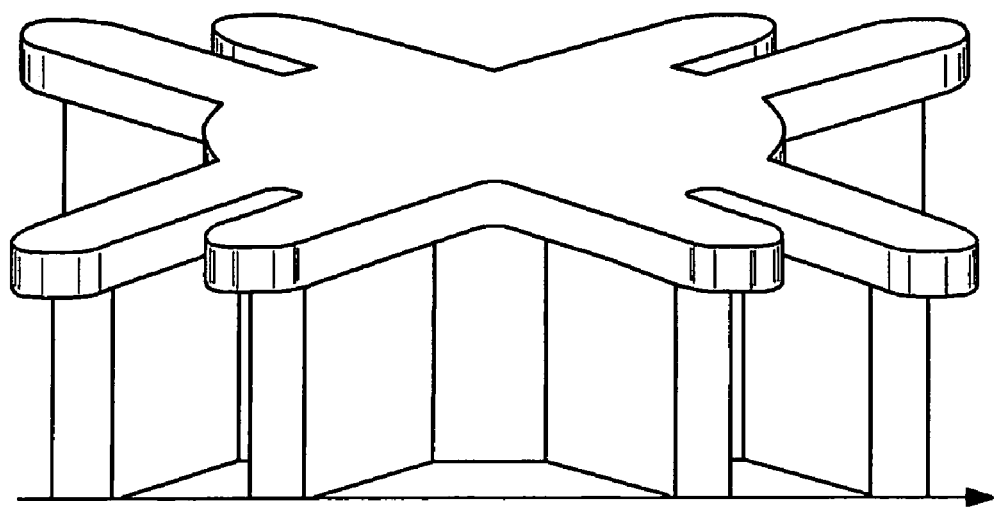

FIGS. 74 and 75 are alternative, multi-direction, multi-pronged fasteners that provide multi-directional engagement from a single stem. Employing thin fin segments formed by tooling similar to that of FIG. 67.

Preferred Process for Production

Figure 76:
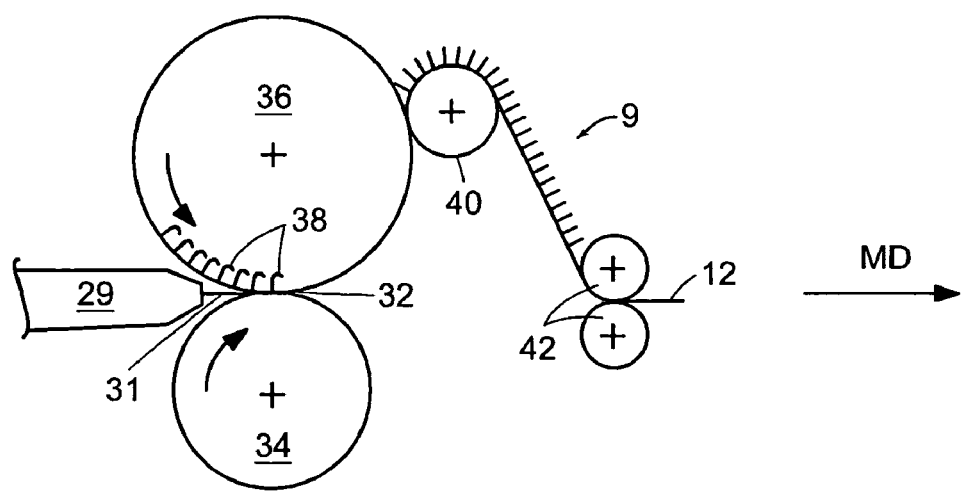
FIGS. 76 and 77 illustrate two machines for making preform sheets.

The preform products shown can be formed by the method and apparatus illustrated in FIG. 76. Thermoplastic resin 31 from extruder 29 is introduced into nip 32 formed between a supporting pressure roll 34 and a mold roll 36. Pressure in the nip causes thermoplastic resin 31 to enter blind-ended stem formation forming cavities 38 of mold roll 36 while excess resin remains about the periphery of the mold roll and is effectively calendared to form base sheet 12. As the rolls 34, 36 rotate in opposite directions (shown by arrows), the thermoplastic resin proceeds along the periphery of the mold roll until it is stripped from both the mold cavities and the roll periphery by stripper roll 40. The resulting product has base 12 with integrally formed stem formations with sets of small features as described above. The direction of travel of the material illustrated in FIG. 76 is referred to as the "machine direction" (MD) of the material and defines the longitudinal direction of the resulting preform product.

In preferred cases, the mold roll comprises a face-to-face assemblage of circular plates or rings, some having cutouts in their periphery defining mold cavities and others being circular, serving to close the open sides of the mold cavities and serve as spacers.

Once preform product 9 has been stripped from mold roll 36, it proceeds through guide rolls 42 to a head shaping station where the loop engageable heads are formed as described above.

Figure 77:
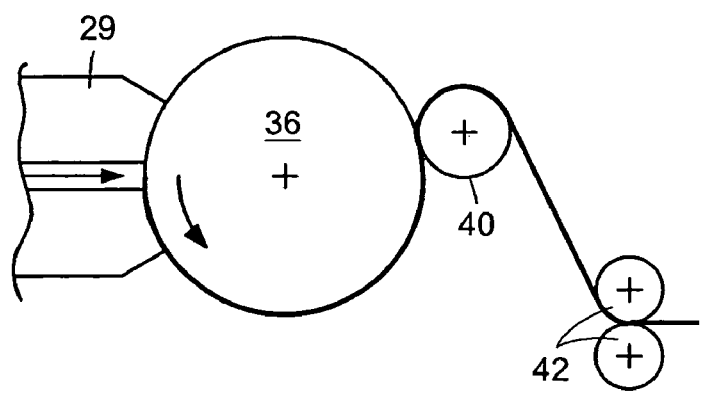

In another embodiment, illustrated in FIG. 77, an alternate technique for producing preform stem product 9 is employed. The process is similar to that described above with reference to FIG. 76, except only a mold roll is used, i.e., no pressure roll is necessary. Here, the extruder head 29 is shaped to conform to the periphery of the mold roll and the extruded resin 31 is introduced directly to a gap formed between the mold roll and the extruder head. From here, the preform stems on the sheet-form base go to the head shaping station where the loop engageable heads are formed as described above.

Figure 78:
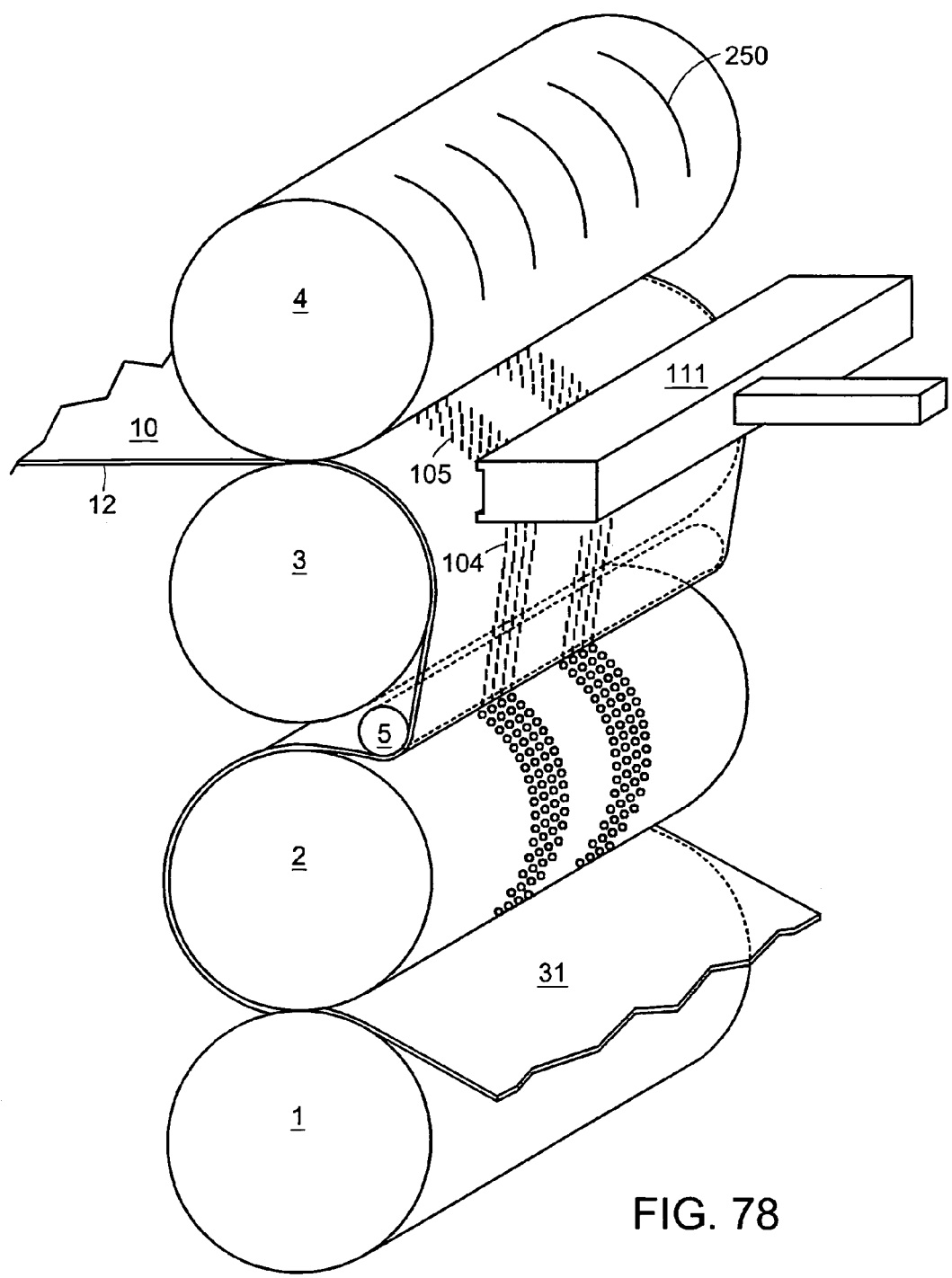
FIG. 78 is a perspective view of a preferred apparatus for making fastener members of the types illustrated in preceding figures.

The presently preferred method for forming fastener product 10 is shown in FIG. 78. Extruder 29 (not shown) provides a traveling molten resin strip to a roll stack comprised of rolls 1, 2, 3 and 4, numbering from bottom to top. The plastic passes through the nip between rolls 1 and 2. Roll 2 is a mold roll, its exposed outer surface includes mold cavities such that the molten polymer flowing into the cavities takes on the form of the cavity and then is demolded to provide preform stems of substantially unoriented resin. It is one of the features of this invention that, by the use of non-contact heating, advantage is taken of the unoriented nature of the polymer to enable surface tension effects to act to strategically locate and size the deformable mass of polymer so that highly desirable effects are obtainable by the "flat-topping" i.e. press-forming action.

An array of stems integral with a backing sheet, with extent in both X and Y directions is thus molded by roll 2, and the stems are demolded about a take-off roller 5 (FIG. 78) in making the transition to roll 3. On roll 3, close to the nip with conformation roll 4, the end portion of the stems pass under a non-contact heat source as a first step to create the hook heads.

In this embodiment, the non-contact heat source is a close-lying gas burner 111, and the sides as well as the ends of terminal tip portions of the prongs or other small features are immersed in the hot gases produced by the burner. Thus the sides are rapidly heated by convective effects as are the top portions, which also receive radiative heating. Given the high surface area exposed to the intense heat, compared to the bounded volume of resin of the exposed terminal portion of the structure, these small portions are rapidly melted, with highest temperature and lowest viscosity achieved at the terminal ends.

In this condition, the stems pass between another nip created between rolls 3 and 4, in which roll 4 presses down upon the molten polymer terminal ends and forms a flattened head shape, to form heads of shape depending upon the characteristics of this roll and the degree of compaction produced on the ends of the features.

Preferably, the forming roll 4 is cooled, to remain at a temperature below the molten polymer temperature, preferably considerably lower.

With the surface of roll 4 cooled to temperature below the condensation temperature of steam, and in the case of use of flame from a burner to heat the stems in close proximity to a cooled conformation roll 4, water 250 as a combustion product from the burning gas fuel condenses on the roll 4 and is found to act as a release agent for promoting clean separation of the formed heads and the surface of the roll as the headed hooks exit from under the forming roll. (Likewise, steam or water mist may be introduced to the roll, as the case of using non-flame radiant heating.) In such cases both the cool temperature of the conformation roll 4 and the moisture promote clean release of the heads from the roll surface without sticking of the heads to the roll. Best advantage is obtained by locating the point of heating close to the roll. In preferred embodiments the tip of the burner is within one centimeter of roll 3 and within 2½ centimeters of roll 4, adjustment of the separation of the burner from roll 3 serving as a control for the amount of convective heating obtained.

The air gas mixture of the gaseous fuel and air is introduced to the burner in substantially stoichiometric ratio for optimum combustion, such that substantially complete combustion occurs, producing byproducts essentially only of carbon dioxide and water.

The burner may have a ribbon opening extending across the width of the web, or may comprise jet holes, the spacing between holes being closer than the distance to the heads such that because of air entrainment a substantially uniform turbulent stream of hot gas reaches the top portion of the features to be melted.

In one preferred embodiment a ribbon burner is used, providing a continuous line of flame. The burner temperature is between about 1000° and 1200° C., produced with a natural gas feed, the primary component of which is methane ($CH_4$).

The burner face is approximately 1" wide. The web carrying the stem preform travels at speeds in the range of 20 to 200 ft/min (depending upon the product desired and operating parameters), and so a stem preform element spends only a fraction of a second under the burner. In this amount of time a sufficient amount of heat is transferred into the preform element to enable it to be deformed into a hook. Heat is transferred to the preform element by forced convection. Heat is transferred through the tops of the small features as well as sides. The amount of heat transferred to the preform element, is controlled by the position of the burner relative to the elements.

Simple steps may be followed in set-up for such flat-topping.

1. Extrude and form a web of preform stems on a continuous backing, as described above.
2. Set gap position of the forming roll (Gap between rolls 3 and 4) at a position that corresponds with desired hook height while stem forming is occurring. At this point stems passing through the gap will buckle since their tips are not being heated.

3. Turn on the burner and, step-wise, bring the burner closer to the terminal ends of the stems. The burner position will typically vary from 0.2" to 1" from roll 4. The flame set-up (i.e. flow conditions) is maintained constant, so that the only variable altered is the position of the burner with respect to roll 3.

In some cases the line speed is dependent upon the amount of heat desired to be transferred to the stems. For instance, comparing 2 sets of stems, Group A is smaller than Group B. Group B requires more heat per stem, and passing heat through a larger body requires more time for heat to be transferred such that Group B may run at a speed ⅓ that of Group A.

The mold cavities in roll 2 are formed by rings that are placed face-to-face together in registry such that when viewed from a plan view down upon the periphery of the mold ring pair, a plus sign mold shape is provided. Many sets of rings are placed side-by-side and pressed onto a shaft, providing an axial distribution of peripheral rows of cavities. The size of the cavities and their distribution is selected according to the needs of the particular fastening system being constructed. Typically, a slight draft angle, e.g. of 1°, is employed to enable the molded prongs or other features to readily leave its mold. As shown, solid spacer rings having no mold cavities are placed between pairs of rings.

A number of embodiments of the invention have been described. Nevertheless, it will be understood that various modifications may be made without departing from the spirit and scope of the invention. Accordingly, other embodiments are within the scope of the following claims.

What is claimed is:

1. A method of forming a fastener component having heads constructed to engage loops formed of fibers of a mating component, comprising:
   forming, from a thermoformable material, a preform product having a strip-form base and an array of preform stems integrally molded with and extending from the base to corresponding, distal ends, the fastener component defining both a machine direction, extending along a major length of the strip-form base, and a cross-machine direction, each molded stem having at least two upright features spaced from one another in the cross-machine direction, the features each having a thickness of about 0.1 mm (0.004 inch) or less, and
   heating terminal ends of the features to a predetermined softening temperature, while maintaining the strip-form base and a lower portion of each stem at a temperature lower than the softening temperature, and contacting the terminal ends with a contact surface that is at a predetermined forming temperature to at least assist in reforming the terminal ends to form head portions therefrom that overhang the strip-form base sufficiently to engage loops, the geometry and material of the preform product and the condition of reforming the terminal ends of the upright features being so related that the formed head portions are capable of peel-resistant engagement with loops of nonwoven fabrics.

2. The method of claim 1 in which said upright features extend straight, not overhanging the base layer.

3. The method of claim 1 in which each molded stem also has at least two upright features spaced from one another in the machine direction.

4. The method of claim 1 in which the molded preform stems have substantially parallel side surfaces on all sides.

5. The method of claim 4 in which the parallel sides extend perpendicular to the strip-form base.

6. The method of claim 1 in which the molded stems are of substantially "M" or crossed "M" profile.

7. The method of claim 6 in which said molded stems are bifurcated, trifurcated or otherwise effectively divided into multiple segments each having a distal portion with features to be deformed.

8. The method of claim 1 in which the molded stems are of substantially thin fin or crossed thin fin form, lateral ends of the fins comprising said upright features.

9. The method of claim 1 in which the molded stems carry upwardly directed, spaced apart prongs that define said upright features.

10. The method of claim 9 in which at least one prong has dimensions different from another prong selected to form a different head shape.

11. The method of claim 10 in which at least one prong has a terminal end spaced further from said strip-form base than another prong.

12. The method of claim 10 in which at least one prong has a transverse dimension different from another prong.

13. The method of claim 9 in which a stem has at least three prongs arranged along at least one direction.

14. The method of claim 9 in which a separate fiber-engaging head is formed on a terminal end of each prong.

15. The method of claim 9 in which head portions of a group of at least two neighboring prongs are coalesced to form portions of a single head.

16. The method of claim 9 in which head portions of substantially all prongs of a stem are coalesced to form portions of a single head.

17. The method of claim 9 in which in transverse cross-section the prongs have a rectangular profile.

18. The method of claim 9 which in transverse cross-section the prongs have a round profile.

19. The method of claim 1 in which at least one of said upright features is shaped and arranged to be displaced laterally during formation of said head portions.

20. The method of claim 1 in which the terminal ends of the features are heated by non-contact heating.

21. The method of claim 20 in which said non-contact heat source comprises a convective heat source.

22. The method of claim 21 in which the convective heat source comprises a flame.

23. The method of claim 1 in which the preform stems and the features thereon are formed from a synthetic polymer, the polymer being molecularly unoriented.

24. The method of claim 1 in which the step of heating the terminal ends of the features to a predetermined softening temperature forms ball-like configurations at the distal ends of the stems.

25. The method of claim 1 in which the temperature of said contact surface is sufficiently low that said thermoformable material does not adhere to the contact surface.

26. The method of claim 1 in which liquid water, water of combustion or steam is introduced to the contact surface to provide a non-adhering agent.

27. The method of claim 1 in which the reforming is performed with a cool roll that sets the form of said head portions.

28. The method of claim 1 in which the terminal ends are super heated and the resin flows into the final form of said head portions.

29. A method of making a touch fastener, the method comprising:
  continuously molding a plurality of stems extending outwardly from, continuous with and substantially perpendicular to, a sheet-form base continuous in a longitudinal direction, each stem having a distal top, a central portion, a stem base, the intersection of the stem base and the sheet form base defining a base region, and a plurality of uptight features, each having a thickness of about 0.1 mm (0.004 inch) or less, extending outwardly from and continuous with the central portion, wherein the features comprise a multiplicity of prongs that extend from the top of the stem and are spaced apart in the longitudinal direction, and
  forming loop engageable elements at tops of the features.

30. The method of claim 29 in which the features extend laterally from the central portion of the stem.

31. The method of claim 29 wherein the thickness is about 0.20 mm (0.008 inch) or less.

32. The method of claim 29 wherein the thickness is about 0.10 mm (0.004 inch) or less.

33. The method of claim 29 in which each molded stem also has at least two upright features spaced from one another in the machine direction.

34. The method of claim 29 in which the molded preform stems have substantially parallel side surfaces on all sides.

35. The method of claim 29 in which the molded stems are of substantially "M" or crossed "M" profile.

36. The method of claim 29 in which at least one prong has dimensions different from another prong selected to form a different head shape.

37. The method of claim 29 in which at least one prong has a terminal end spaced further from said strip-form base than another prong.

38. The method of claim 29 in which at least one prong has a transverse dimension different from another prong.

39. The method of claim 29 in which a stem has at least three prongs arranged along at least one direction.

40. The method of claim 29 in which a separate fiber-engaging head is formed on a terminal end of each prong.

41. The method of claim 29 in which head portions of a group of at least two neighboring prongs are coalesced to form portions of a single head.

42. The method of claim 29 in which head portions of substantially all prongs of a stem are coalesced to form portions of a single head.

43. A method of forming a fastener component having heads constructed to engage loops formed of fibers of a mating component, comprising:
  forming, from a thermoformable material, a preform product having a strip-form base and an array of preform stems integrally molded with and extending from the base to corresponding, distal ends, the fastener component defining both a machine direction, extending along a major length of the strip-form base, and a cross-machine direction, each molded stem having at least two upright features spaced from one another in the cross-machine direction and, the features each having a thickness of about 0.25 mm (0.0 10 inch) or less, wherein the molded stems are of substantially "M" or crossed "M" profile, the upright features comprising tips of the "M" profile, and
  heating terminal ends of the features to a predetermined softening temperature, while maintaining the strip-form base and a lower portion of each stem at a temperature lower than the softening temperature, and contacting the terminal ends with a contact surface that is at a predetermined forming temperature to at least assist in reforming the terminal ends to form head portions therefrom that overhang the strip-form base sufficiently to engage loops, the geometry and material of the preform product and the condition of reforming the terminal ends of the upright features being so related that the formed head portions are capable of peel-resistant engagement with loops of nonwoven fabrics.

44. The method of claim 43 in which said molded stems are bifurcated, trifurcated or otherwise effectively divided into multiple segments each having a distal portion with features to be deformed.

45. The method of claim 43 wherein the thickness is about 0.20 mm (0.008 inch) or less.

46. The method of claim 43 wherein the thickness is about 0.10 mm (0.004 inch) or less.

47. A method of forming a fastener component having heads constructed to engage loops formed of fibers of a mating component, comprising:
  forming, from a thermoformable material, a preform product having a strip-form base and an array of preform stems integrally molded with and extending from the base to corresponding, distal ends, the fastener component defining both a machine direction, extending along a major length of the strip-form base, and a cross-machine direction, each molded stem having at least two upright features spaced from one another in the cross-machine direction, the features each having a thickness of about 0.25 mm (0.010 inch) or less, and heating terminal ends of the features to a predetermined softening temperature to form ball-like configurations at the distal ends of the stems, while maintaining the strip-form base and a lower portion of each stem at a temperature lower than the softening temperature, and contacting the terminal ends with a contact surface that is at a predetermined forming temperature to at least assist in reforming the terminal ends to form head portions therefrom that overhang the strip-form base sufficiently to engage loops, the geometry and material of the preform product and the condition of reforming the terminal ends of the upright features being so related that the formed head portions are capable of peel-resistant engagement with loops of nonwoven fabrics.

48. The method of claim 47 wherein the thickness is about 0.20 mm (0.008 inch) or less.

49. The method of claim 47 wherein the thickness is about 0.10 mm (0.004 inch) or less.

50. The method of claim 47 in which the molded preform stems have substantially parallel side surfaces on all sides.

51. A method of forming a fastener component having heads constructed to engage loops formed of fibers of a mating component, comprising:
  forming, from a thermoformable material, a preform product having a strip-form base and an array of preform stems integrally molded with and extending from the base to corresponding, distal ends, the fastener component defining both a machine direction, extending along a major length of the strip-form base, and a cross-machine direction, each molded stem having at least two upright features spaced from one another in the cross-machine direction, the features each having a thickness of about 0.25 mm (0.010 inch) or less, and super-heating terminal ends of the features to a predetermined softening temperature, while maintaining the strip-form base and a lower portion of each stem at a temperature lower than the softening temperature, and contacting the terminal ends with a contact surface that is at a predetermined forming temperature to at least assist in reforming the terminal ends to form head portions therefrom that overhang the strip-form base sufficiently to engage loops, the resin flowing after said contacting into final form, the geometry and material of the preform product and the condition of reforming the terminal ends of the upright features being so related that the formed head portions are capable of peel-resistant engagement with loops of nonwoven fabrics.

52. The method of claim 51 wherein the thickness is about 0.20 mm (0.008 inch) or less.

53. The method of claim 51 wherein the thickness is about 0.10 mm (0.004 inch) or less.

54. The method of claim 51 in which said upright features extend straight, not overhanging the base layer.

55. The method of claim 51 in which each molded stem also has at least two upright features spaced from one another in the machine direction.

56. The method of claim 51 in which the molded preform stems have substantially parallel side surfaces on all sides.

57. The method of claim 56 in which the parallel sides extend perpendicular to the strip-form base.

* * * * *

UNITED STATES PATENT AND TRADEMARK OFFICE
CERTIFICATE OF CORRECTION

PATENT NO.          : 7,052,638 B2                                    Page 1 of 1
APPLICATION NO. : 10/455240
DATED               : May 30, 2006
INVENTOR(S)         : Mark A. Clarner, George A. Provost and William L. Huber It is certified that error appears in the above-identified patent and that said Letters Patent is hereby corrected as shown below:

Title Page, Assignee (73): Change "Curacan" to --Curacao--

Title Page, REFERENCES CITED – OTHER PUBLICATIONS (56): delete "US 6,129,874 10/2000, Buzzell et al. (withdrawn)"

Title Page, REFERENCES CITED – U.S. PATENT DOCUMENTS (56): add -- US 6,129,874 10/2000, Buzzell et al. (withdrawn)--

Signed and Sealed this

Sixth Day of November, 2007

JON W. DUDAS
*Director of the United States Patent and Trademark Office*